(12) United States Patent
Toledano et al.

(10) Patent No.: US 8,617,580 B2
(45) Date of Patent: Dec. 31, 2013

(54) COMPOSITIONS FOR TOPICAL APPLICATION COMPRISING A PEROXIDE AND RETINOID

(75) Inventors: Ofer Toledano, Kfar-Saba (IL); Hanan Sertchook, Gedera (IL); Natalia Loboda, Jerusalem (IL); Haim Bar-Simantov, Modiin (IL); Leora Shapiro, Jerusalem (IL); Raed Abu-Reziq, Jatt Hamesholash (IL)

(73) Assignee: Sol-Gel Technologies Ltd., Ness Ziona (IL)

( * ) Notice: Subject to any disclaimer, the term of this patent is extended or adjusted under 35 U.S.C. 154(b) by 0 days.

(21) Appl. No.: 13/495,701

(22) Filed: Jun. 13, 2012

(65) Prior Publication Data

US 2012/0269874 A1 Oct. 25, 2012

Related U.S. Application Data

(63) Continuation of application No. 12/525,329, filed as application No. PCT/IL2008/000140 on Feb. 3, 2008, now abandoned.

(60) Provisional application No. 60/898,701, filed on Feb. 1, 2007.

(51) Int. Cl.
*A61Q 19/02* (2006.01)
*A61P 17/10* (2006.01)

(52) U.S. Cl.
USPC ............................................. 424/401

(58) Field of Classification Search
None
See application file for complete search history.

(56) References Cited

U.S. PATENT DOCUMENTS

| | | | |
|---|---|---|---|
| 2,885,366 A | 5/1959 | Iler | |
| 3,785,798 A | 1/1974 | Horai et al. | |
| 3,826,670 A | 7/1974 | Rees et al. | |
| 3,957,971 A | 5/1976 | Oleniacz | |
| 4,129,645 A | 12/1978 | Barnett et al. | |
| 4,169,069 A | 9/1979 | Unger et al. | |
| 4,349,456 A | 9/1982 | Sowman | |
| 4,350,681 A | 9/1982 | Fulton, Jr. | |
| 4,361,584 A | 11/1982 | Fulton, Jr. | |
| 4,387,107 A | 6/1983 | Klein et al. | |
| 4,444,746 A | 4/1984 | Harvey et al. | |
| 4,464,317 A | 8/1984 | Thies et al. | |
| 4,497,794 A | 2/1985 | Klein et al. | |
| 4,606,913 A | 8/1986 | Aronson et al. | |
| 4,671,956 A | 6/1987 | Bouillon et al. | |
| 4,686,211 A | 8/1987 | Hara et al. | |
| 4,690,825 A | 9/1987 | Won | |
| 4,692,329 A | 9/1987 | Klein et al. | |
| 4,769,080 A | 9/1988 | Clark et al. | |
| 4,891,211 A | 1/1990 | Winston | |
| 4,931,362 A | 6/1990 | Zsifkovits et al. | |
| 4,960,772 A | 10/1990 | Sebag et al. | |
| 4,988,744 A | 1/1991 | Yamamoto | |
| 5,086,075 A | 2/1992 | De Villez | |
| 5,126,915 A | 6/1992 | Pepin et al. | |
| 5,145,675 A | 9/1992 | Won | |
| 5,165,914 A | 11/1992 | Vlock | |
| 5,200,334 A | 4/1993 | Dunn et al. | |
| 5,223,250 A | 6/1993 | Mitchell et al. | |
| 5,269,840 A | 12/1993 | Morris et al. | |
| 5,292,801 A | 3/1994 | Avnir et al. | |
| 5,387,622 A | 2/1995 | Yamamoto | |
| 5,446,028 A | 8/1995 | Klein et al. | |
| 5,455,048 A | 10/1995 | Lahmani et al. | |
| 5,466,446 A | 11/1995 | Stiefel et al. | |
| 5,472,491 A | 12/1995 | Duschek et al. | |
| 5,500,223 A | 3/1996 | Behan et al. | |
| 5,520,917 A | 5/1996 | Mizuguchi et al. | |
| 5,556,617 A | 9/1996 | Ribier et al. | |
| 5,587,170 A | 12/1996 | Caisey et al. | |
| 5,591,453 A | 1/1997 | Ducheyne et al. | |
| 5,607,664 A | 3/1997 | Ascione et al. | |
| 5,632,996 A | 5/1997 | Ramirez et al. | |
| 5,635,609 A | 6/1997 | Levy et al. | |
| 5,650,311 A | 7/1997 | Avnir et al. | |
| 5,670,209 A | 9/1997 | Wyckoff | |
| 5,672,301 A | 9/1997 | Orly et al. | |
| 5,691,060 A | 11/1997 | Levy | |
| 5,700,451 A | 12/1997 | Yue et al. | |
| 5,733,531 A | 3/1998 | Mitchnick et al. | |

(Continued)

FOREIGN PATENT DOCUMENTS

| AU | 199963469 | 5/2000 |
|---|---|---|
| AU | 764016 | 5/2002 |

(Continued)

OTHER PUBLICATIONS

Iskandar et al., "Control of the morphology of nanostructured particles prepared by the spray drying of a nanoparticle sol," *Journal of Colloid and Interface Science*, vol. 265, pp. 296-303, 2003.

(Continued)

Primary Examiner — David J Blanchard
Assistant Examiner — Sarah Chickos
(74) Attorney, Agent, or Firm — Oliff & Berridge, PLC

(57) ABSTRACT

The invention relates to a composition for topical application comprising as an active ingredient a peroxide and a retinoid wherein one of said peroxide and retinoid is in the form of first microparticles comprising a solid particulate matter of the active ingredient coated by a metal oxide layer and the other of said peroxide and retinoid is present in an uncoated free form or in a coated form of the active ingredient. The invention further relates to method for treating a surface condition in a subject using said composition, a method for preparing a composition exhibiting improved stability, and a kit comprising: (a) a first composition comprising a peroxide as a first active ingredient; and (b) a second composition comprising a retinoid as a second active ingredient; at least one of said first and said second active ingredient being coated by a metal oxide layer.

19 Claims, 3 Drawing Sheets

(56) References Cited

U.S. PATENT DOCUMENTS

| | | |
|---|---|---|
| 5,739,020 A | 4/1998 | Pope |
| 5,767,098 A | 6/1998 | Klein et al. |
| 5,785,977 A | 7/1998 | Breithbarth |
| 5,792,250 A | 8/1998 | Braun et al. |
| 5,851,538 A | 12/1998 | Froix et al. |
| 5,874,105 A | 2/1999 | Watkins et al. |
| 5,876,699 A | 3/1999 | DiSomma et al. |
| 5,879,716 A | 3/1999 | Katz et al. |
| 5,895,757 A | 4/1999 | Pope |
| 5,906,811 A | 5/1999 | Hersh |
| 5,912,016 A | 6/1999 | Perrier et al. |
| 5,914,101 A | 6/1999 | Tapley et al. |
| 5,932,228 A | 8/1999 | Hall et al. |
| 5,955,109 A | 9/1999 | Won et al. |
| 5,962,517 A | 10/1999 | Murad |
| 5,998,392 A | 12/1999 | Simard et al. |
| 6,013,637 A | 1/2000 | Klein et al. |
| 6,015,548 A | 1/2000 | Siddiqui et al. |
| 6,074,629 A | 6/2000 | Kostinko |
| 6,077,522 A | 6/2000 | Scher et al. |
| 6,090,399 A | 7/2000 | Ghosh et al. |
| 6,096,765 A | 8/2000 | Bershad |
| 6,103,267 A | 8/2000 | Mitchnick et al. |
| 6,117,843 A | 9/2000 | Baroody et al. |
| 6,132,773 A | 10/2000 | Amiche |
| 6,143,280 A | 11/2000 | Pike et al. |
| 6,146,664 A | 11/2000 | Siddiqui |
| 6,159,453 A | 12/2000 | Avnir et al. |
| 6,171,600 B1 | 1/2001 | Dahms |
| 6,197,757 B1 | 3/2001 | Perrier et al. |
| 6,200,375 B1 | 3/2001 | Guez et al. |
| 6,217,852 B1 | 4/2001 | Gildenberg et al. |
| 6,238,650 B1 | 5/2001 | Lapidot et al. |
| 6,242,099 B1 | 6/2001 | Grandmontagne et al. |
| 6,251,313 B1 | 6/2001 | Deubzer et al. |
| 6,280,746 B1 | 8/2001 | Arquette et al. |
| 6,303,149 B1 | 10/2001 | Magdassi et al. |
| 6,303,290 B1 | 10/2001 | Liu et al. |
| 6,337,089 B1 | 1/2002 | Yoshioka et al. |
| 6,436,375 B1 | 8/2002 | Lapidot et al. |
| 6,468,509 B2 | 10/2002 | Lapidot et al. |
| 6,479,146 B1 | 11/2002 | Caruso et al. |
| 6,495,352 B1 | 12/2002 | Brinker et al. |
| 6,534,044 B1 | 3/2003 | Wada et al. |
| 6,537,583 B1 | 3/2003 | Dupuis et al. |
| 6,607,713 B1 | 8/2003 | Chodorowski et al. |
| 6,616,947 B1 | 9/2003 | Depuis |
| 6,646,947 B2 | 11/2003 | Fukui et al. |
| 6,703,032 B2 | 3/2004 | Gers-Barlag et al. |
| 6,855,335 B2 | 2/2005 | Seok et al. |
| 6,875,264 B2 | 4/2005 | Zimmermann et al. |
| 6,913,825 B2 | 7/2005 | Ostafin et al. |
| 7,001,592 B1 | 2/2006 | Traynor et al. |
| 7,037,513 B1 | 5/2006 | Traynor et al. |
| 7,052,913 B2 | 5/2006 | Babich et al. |
| 7,758,888 B2 | 7/2010 | Lapidot et al. |
| 8,039,020 B2 | 10/2011 | Lapidot et al. |
| 2002/0064541 A1 | 5/2002 | Lapidot et al. |
| 2002/0151527 A1 | 10/2002 | Wiegand et al. |
| 2002/0193321 A1 | 12/2002 | Vishnupad et al. |
| 2003/0004118 A1 | 1/2003 | Vishnupad et al. |
| 2003/0170196 A1 | 9/2003 | Orsoni et al. |
| 2005/0037087 A1 | 2/2005 | Lapidot et al. |
| 2005/0208134 A1 | 9/2005 | Magdassi et al. |
| 2005/0276807 A1 | 12/2005 | Skurkovich et al. |
| 2006/0251687 A1 | 11/2006 | Lapidot et al. |
| 2007/0003585 A1 | 1/2007 | Clark et al. |
| 2007/0292676 A1 | 12/2007 | Naigertsik et al. |

FOREIGN PATENT DOCUMENTS

| | | |
|---|---|---|
| DE | 44 16 003 | 11/1995 |
| DE | 19811900 | 9/1999 |
| EP | 0281034 | 9/1988 |
| EP | 0462388 | 12/1991 |
| EP | 0581651 | 2/1994 |
| EP | 0680753 | 11/1995 |
| EP | 0 934 773 A2 | 8/1999 |
| EP | 0 941 761 A2 | 9/1999 |
| EP | 0972563 | 1/2000 |
| EP | 1 116 516 | 7/2001 |
| FR | 2703927 | 10/1994 |
| FR | 2774906 | 8/1999 |
| FR | 2780901 | 1/2000 |
| FR | 2 833 841 | 12/2001 |
| GB | 1399344 | 7/1975 |
| GB | 2 416 524 A | 2/2006 |
| JP | A-02-002867 | 1/1990 |
| JP | A-2040302 | 2/1990 |
| JP | A-02-251240 | 10/1990 |
| JP | A-02-292824 | 12/1990 |
| JP | A-03-243663 | 10/1991 |
| JP | A-03229634 | 10/1991 |
| JP | A-05-043208 | 2/1993 |
| JP | A-07173452 | 7/1995 |
| JP | A-09110463 | 4/1997 |
| JP | A-09-235217 | 9/1997 |
| JP | A-01-113436 | 2/1998 |
| JP | A-2003-534249 | 11/2003 |
| JP | A-2005-513146 | 5/2005 |
| JP | A-2005-528152 | 9/2005 |
| JP | A-2005-529636 | 10/2005 |
| RU | 98105780 | 12/1999 |
| WO | WO 9404260 | 3/1994 |
| WO | WO 9404261 | 3/1994 |
| WO | WO 97/07676 | 3/1997 |
| WO | WO 9732561 | 9/1997 |
| WO | WO 9740106 | 10/1997 |
| WO | WO 9745367 | 12/1997 |
| WO | WO 98/15183 | 4/1998 |
| WO | WO 9831333 | 7/1998 |
| WO | WO 9903450 | 1/1999 |
| WO | WO 99/47253 | 9/1999 |
| WO | WO 00/09652 A2 | 2/2000 |
| WO | WO 0025761 | 5/2000 |
| WO | WO 0025781 | 5/2000 |
| WO | WO 0025908 | 5/2000 |
| WO | WO 0047236 | 8/2000 |
| WO | WO 00/71084 A1 | 11/2000 |
| WO | WO 00/72806 A2 | 12/2000 |
| WO | WO 0112221 | 2/2001 |
| WO | WO 0113924 | 3/2001 |
| WO | WO 01/058451 A1 | 8/2001 |
| WO | WO 01/80823 A2 | 11/2001 |
| WO | WO 02/085113 | 10/2002 |
| WO | WO 03/003497 A1 | 1/2003 |
| WO | WO 03/034973 | 5/2003 |
| WO | WO 03/039510 A1 | 5/2003 |
| WO | WO 03/066209 A1 | 8/2003 |
| WO | WO 03/086419 A1 | 10/2003 |
| WO | WO 03/099295 A1 | 12/2003 |
| WO | WO 03/104319 | 12/2003 |
| WO | WO 2004/064769 A2 | 8/2004 |
| WO | WO 2004/064803 A1 | 8/2004 |
| WO | WO 2004/069135 A2 | 8/2004 |
| WO | WO 2004/069216 | 8/2004 |
| WO | WO 2004/081222 A2 | 9/2004 |
| WO | WO 2005/009604 A1 | 2/2005 |
| WO | WO 2007/000316 | 1/2007 |
| WO | WO 2007/015243 A2 | 2/2007 |
| WO | WO 2007036939 | 2/2007 |
| WO | WO 2008/002637 | 1/2008 |
| WO | WO 2008/093346 | 8/2008 |
| WO | WO 2008/093347 | 8/2008 |

OTHER PUBLICATIONS

Iskandar et al., "Preparation of microencapsulated powders by an aerosol spray method and their optical properties," *Advanced Powder Technologies*, vol. 14, No. 3, pp. 349-367, 2003.

Tatapudy et al., "Benzoyl Peroxide Microcapsules I. Preparation of Core Material," *Indian Drugs*, vol. 32, No. 6, pp. 239-248, 1995.

(56) References Cited

OTHER PUBLICATIONS

"Martindale: The extra Pharmacopeia," *Pharmaceutical Press*, pp. 1093-1095, 1999.
Wenninger et al., *International Cosmetic Ingredient Dictionary and Handbook*, Eighth Edition 2000, vol. 2, Published by The Cosmetic, Toiletry, and Fragrance Association, pp. 1140-1147.
Kortesuo et al., "In vitro evaluation of sol-gel processed spray dried silica gel microspheres as carrier in controlled drug delivery," *International Journal of Pharmaceutics*, vol. 200, pp. 223-229, 2000.
Kortesuo et al., "Effect of synthesis parameters of the sol-gel-processed spray-dried silica gel microparticles on the release rate of dexmedetomidine," *Biomaterials*, vol. 23, pp. 2795-2801, 2002.
Takeuchi et al., "Solid dispersion particles of tolbutamide prepared with fine silica particles by the spray-drying method," *Powder Technology*, vol. 141, pp. 187-195, 2004.
International Search Report issued in Application No. PCT/IL2008/000140; Dated Apr. 16, 2009.
Oct. 9, 2007 Office Action issued in U.S. Appl. No. 09/983,229.
Jul. 22, 2008 Office Action issued in U.S. Appl. No. 09/983,229.
Final Office Action issued in connection with U.S. Appl. No. 10/566,369 on Jan. 3, 2011.
Apr. 28, 2009 Office Action issued in U.S. Appl. No. 09/983,229.
U.S. Appl. No. 90/011,440, filed Jan. 18, 2011 to Lapidot et al.
Aizawa, et al., "Preparation of Spherical Hydrous Silica Oxide Particles under Acidic Condition via Sol-Gel Processing", Journal of Sol-Gel Science and Technology, (2000),19:329-332.
Butler, et al., "An Emulsion Method for Producing Fine, Low Density, High Surface Area Silica Powder from Alkoxides", Journal of Material Science, (1996), 31 :1675-1680.
Nakatsuka, et al., "Surface Modification of Inorganic Pigments with Organic UV Absorbers", Colloid Surface, (1988/1989), 34:323-334.
Mar. 10, 2010 Notice of Allowance issued in U.S. Appl. No. 09/983,229.
Hench, et al., "The Sol-Gel Process", Chem. Rev. 1990, vol. 90, pp. 33-72.
Sol-Gel Science, The Physics and Chemistry of Sol-Gel Processing, C. Jeffrey Brinker, George W. Scherer, May 1990, (pp. 562-563).
Bugnon, P., "Surface treatment of pigments. Treatment with inorganic materials", Progress in Organic Coatings, vol. 29, pp. 39-43, (1996).
Hall, S., et al., "Cocondensation of Organosilica Hybrid Shells on Nanoparticle, Templates: A Direct Synthetic Route to Functionalized Core—Shell Colloids", Langmuir, vol. 16, pp. 1454-1456, (2000).
Haq et al., "Preparation and properties of uniform coated inorganic colloidal particles 9. Titania on copper 21 compounds", Colloids and Surfaces A: Physicochemical and Engineering Aspects, vol. 81, pp. 153-159, (1993).
Hsu et al., "Paper Whiteners I. Titania Coated Silica", Journal of Colloid and Interface Science, vol. 156, pp. 56-65, (1993).
Iler, R., "Silica Gels", The Chemistry of Silica, pp. 510-533, (1979).
Lapidot, et al., "Advanced Sunscreens: UV Absorbers Encapsulated in Sol-Gel Glass Microcapsules", Journal of Sol-Gel Science and Technology, pp. 67-72, vol. 26, (2003).
Mikrajuddin, et al., "Stable photoluminescence of zinc oxide quantum dots in silica nanoparticles matrix prepared by the combined sol-gel and spray drying method", Journal of Applied Physics, pp. 6431-6434, vol. 89, No. 11, (2001).
Rottman, C., et al., "Advanced Sunscreens: UV Absorbers Entrapped in Glass Microcapsules", Euro Cosmetics, pp. 20-22, (2000).
"Environmental Protection Agency", Federal Register, 2002, vol. 67, No. 94 and 40 CFR part 180, pp. 34616-34620.
Van Bruggen, et al., "Preparation and Properties of Colloidal Core-Shell Rods with Adjustable Aspect Ratios", Langmuir, pp. 2245-2255, vol. 14, No. 9, (1998).
"Ludox TM-50 colloidal silica," Sigma-Aldrich website: http://www.sigmaaaldrich.com/catalog/product/aldrich/420778?lang=en&region=US, downloaded Sep. 7, 2012.

Iler, Ralph K., "The Chemistry of Silica, Solubility, Polymerization, Colloid and Surface Properties, and Biochemistry," John Wiley & Sons, (1979), pp. 366-367.
Zhu-Zhu Li et al., "Fabrication of Porous Hollow Silica Nanoparticles and Their Applications in Drug Release Control," Journal of Controlled Release, (2004) vol. 98, pp. 245-254.
U.S. Appl. No. 11/997,823, filed Sep. 9, 2008, by Toledano et al.
Liz-Marzan et al., "Synthesis of Nanosized Gold-Silica Core-Shell Particles," Langmuir, (1996), pp. 4329-4335, vol. 12.
Beelen et al., "The Role of Aging on the Formation of Porous Silica," Preparation of Catalysts VI, (1995), pp. 33-48, Elsevier Science B.V.
Villalobos et al., "Protective Silica Coatings on Zinc-Sulfide-Based Phosphor Particles", Journal of the American Ceramic Society, 2002, vol. 85, No. 8, pp. 2128-2130.
Wang et al., "Effect of Polyelectrolyte Dispersants on the Preparation of Silica-Coated Zinc Oxide Particles in Aqueous Media", Journal of the American Ceramic Society, 2002, vol. 85, No. 8, pp. 1937-1940.
Wilhelm et al., "On-line tracking of the coating of nanoscaled silica with titania nanoparticles via zeta-potential measurements", Journal of Colloid and Interface Science, 2006, vol. 293, pp. 88-92.
Makarova et al., "Adsorption and Encapsulation of Fluorescent Probes in Nanoparticles", J. Phys. Chem. B, American Chemical Society, 1999, vol. 103, No. 43, pp. 9080-9084.
Merikhi et al., "Adhesion of Colloidal $SiO_2$ Particles on ZnS-Type Phosphor Surfaces", Journal of Colloid and Interface Science, 2000, vol. 228, pp. 121-126.
Rottman et al., "Advanced Sunscreens: UV Absorbers Entrapped in Sol-Gel Glass Microcapsules", Journal of Sol-Gel Science and Technology, pp. 268-270, vol. 23, (2002).
Jean et al., "$Y_2O_2S$:Eu Red Phosphor Powders Coated with Silica", Journal of the American Ceramic Society, 2000, vol. 83, No. 8, pp. 1928-1934.
Dun et al., "Layer-by-Layer Self-Assembly of Multilayer Zirconia Nanoparticles on Silica Spheres for HPLC Packings", Analytical Chemistry, 2004, vol. 76, No. 17, pp. 5016-5023.
Yuan et al., "Organic Pigment Particles Coated with Colloidal Nano-Silica Particles via Layer-by-Layer Assembly", Chem. Mater., 2005, vol. 17, No. 14, pp. 3587-3594.
Kim et al., "Monodisperse hollow titania nanospheres prepared using a cationic colloidal template", Journal of Colloid and Interface Science, 2006, vol. 304, No. 2, pp. 370-377.
Bugosh, "Colloidal Alumina—The Chemistry and Morphology of Colloidal Boehmite", Chemistry and Morphology of Colloidal Boehmite, 1961, vol. 65, pp. 1789-1793.
Chung et al., "Aqueous Synthesis of $Y_2O_2S$: Eu/Silica Core-Shell Particles", Journal of the American Ceramic Society, 2005, vol. 88, No. 5, pp. 1341-1344.
Matijevic et al., "Coating of Nanosize Silver Particles with Silica", Journal of Colloid and Interface Science, 2000, vol. 221, Issue 1, pp. 133-136.
Jun. 6, 2003 Restriction and Election of Species Requirement issued in U.S. Appl. No. 09/983,229.
Mar. 11, 2004 Office Action issued in U.S. Appl. No. 09/983,229.
Dec. 9, 2005 Office Action issued in U.S. Appl. No. 09/983,229.
Aug. 1, 2006 Office Action issued in U.S. Appl. No. 09/983,229.
Jan. 19, 2007 Office Action issued in U.S. Appl. No. 09/983,229.
U.S. Appl. No. 12/525,329, filed Oct. 7, 2009, by Toledano et al.
U.S. Appl. No. 13/243,189, filed Sep. 23, 2011, by Lapidot et al.
U.S. Appl. No. 12/525,331, filed Oct. 6, 2009, by Toledano et al.
U.S. Appl. No. 12/818,924, filed Jun. 18, 2010, by Lapidot et al.
U.S. Appl. No. 9/983,229, filed Oct. 23, 2001, by Lapidot et al.
Dec. 13, 2011 Office Action issued in U.S. Appl. No. 12/525,329.
Oct. 11, 2012 Office Action issued in U.S. Appl. No. 13/243,189.
Jan. 24, 2013 Notice of Allowance issued in U.S. Appl. No. 13/243,189.
Feb. 9, 2012 Office Action issued in U.S. Appl. No. 12/525,331.
May 17, 2012 Office Action issued in U.S. Appl. No. 12/525,331.
Jan. 17, 2013 Office Action issued in U.S. Appl. No. 12/525,331.
Jan. 5, 2011 Office Action issued in U.S. Appl. No. 12/818,924.
Jun. 16, 2011 Notice of Allowance issued in U.S. Appl. No. 12/818,924.

COMPOSITIONS FOR TOPICAL APPLICATION COMPRISING A PEROXIDE AND RETINOID

This is a Continuation of application Ser. No. 12/525,329 filed Jul. 31, 2009, which in turn is a National Stage of Application No. PCT/IL2008/000140 filed Feb. 3, 2008, which claims priority to U.S. Provisional Application No. 60/898,701 filed Feb. 1, 2007. The disclosures of the prior applications are hereby incorporated by reference herein in their entirety.

FIELD OF THE INVENTION

This invention relates to compositions for topical application.

BACKGROUND OF THE INVENTION

Two of the most commonly used ingredients in topical treatments are Benzoyl Peroxide (BPO) and all trans Retinoic acid (Tretinoin (ATRA)) which can be very effective in treating mild to moderate cases of non-inflammatory acne. Benzoyl peroxide acts by destroying *P. acnes*, the bacteria that causes the condition acne. It acts as an antiseptic and as an oxidizing agent, reducing the number of comedones, or blocked pores. Tretinoin (ATRA) is a unique topical medication used in the treatment of acne that allows the keratin plugs of microcomedones to be expelled, thus fewer lesions are able to rupture and cause papules, pustules and nodules of inflammatory acne. A combination drug of BPO and ATRA should have both comedogenesis and bacteriostatic effect in acne treatment. However, two main obstacles to such combination is instability of ATRA in presence of BPO and severe adverse events such as erythema, irritation, burning, stinging, scaling and itching.

Compositions and methods for treatment acne comprising BPO and/or a Retinoid are described for example in U.S. Pat. Nos. 4,350,681, 4,361,584, 4,387,107, 4,497,794, 4,671,956, 4,960,772, 5,086,075, 5,145,675, 5,466,446, 5,632,996, 5,767,098, 5,851,538, 5,955,109, 5,879,716, 5,955,109 5,998,392, 6,013,637, 6,117,843, Pub. No.: US 2003/0170196, US2002064541, and 20050037087. H. Tatapudy et al., Indian Drugs, 32(6), 239-248, 1995, describes benzoyl peroxide microcapsules, prepared by coacervation phase separation process.

Sol-Gel process has been used to encapsulate various active ingredients, thus isolating the active ingredient from the environments.

U.S. Pat. Nos. 6,303,149, 6,238,650, 6,468,509, 6,436,375, US2005037087, US2002064541, and International publication Nos. WO 00/09652, WO00/72806, WO 01/80823, WO 03/03497, WO 03/039510, WO00/71084, WO05/009604, and WO04/81222, disclose sol-gel microcapsules and methods for their preparation. EP 0 934 773 and U.S. Pat. No. 6,337,089 teach microcapsules containing core material and a capsule wall made of organopolysiloxane, and their production. EP 0 941 761 and U.S. Pat. No. 6,251,313 also teach the preparation of microcapsules having shell walls of organopolysiloxane. U.S. Pat. No. 4,931,362 describes a method of forming microcapsules or micromatrix bodies having an interior water-immiscible liquid phase containing an active, water-immiscible ingredient. Microcapsules prepared by a sol-gel process are also disclosed in GB2416524, U.S. Pat. No. 6,855,335, WO03/066209.

There still is a widely recognized need for a composition comprising BPO and retinoid in which the active ingredients are chemically stable when formulated together in the same composition.

SUMMARY OF THE INVENTION

The present invention relates to a composition for topical application comprising as an active ingredient a peroxide and a retinoid wherein one of said peroxide and retinoid is in the form of first microparticles comprising a solid particulate matter of the active ingredient coated by a metal oxide layer and the other of said peroxide and retinoid is present in an uncoated free form or in a coated form of the active ingredient.

The present invention additionally relates to a composition for topical application comprising as an active ingredient benzoyl peroxide and all trans retinoic acid wherein one of said benzoyl peroxide and all trans retinoic acid is in the form of first microparticles comprising a solid particulate matter of the active ingredient coated by a metal oxide layer and the other of said benzoyl peroxide and all trans retinoic acid is present in an uncoated free form or in a coated form of the active ingredient.

The present invention further relates to a composition for topical application comprising as an active ingredient benzoyl peroxide and tazarotene wherein one of said benzoyl peroxide and tazarotene is in the form of first microparticles comprising a solid particulate matter of the active ingredient coated by a metal oxide layer and the other of said benzoyl peroxide and tazarotene is present in an uncoated free form or in a coated form of the active ingredient.

The present invention further relates to a composition for topical application as defined in the present invention said composition having reduced side affects as compared to a reference composition, in which the active ingredients are not coated.

The present invention further relates to a method for treating a surface condition in a subject comprising topically administering onto the surface a composition as described in the present invention.

The present invention additionally relates to a method for preparing a composition comprising as active ingredients a peroxide and a retinoid which are chemically unstable when formulated together, wherein the composition exhibits improved stability of at least one of the active ingredients, the method comprising:

(a) separating said peroxide and retinoid from each other in the composition by coating a solid particulate matter of one of said active ingredients by a metal oxide coating layer to form first microparticles, the other of said peroxide and retinoid is incorporated into the composition in an uncoated free form or in a coated fowl of the active ingredient; and (b) adding excipients for the preparation of the composition.

Further the present invention relates to a kit comprising: (a) a first composition comprising a peroxide as a first active ingredient; and (b) a second composition comprising a retinoid as a second active ingredient; at least one of said first and said second active ingredient being coated by a metal oxide layer.

Moreover the present invention relates to a method of using the kit as described in the present invention wherein said first composition and said second composition are applied concomitantly or sequentially onto a surface of a subject's body.

DETAILED DESCRIPTION OF THE INVENTION

Figure 1:
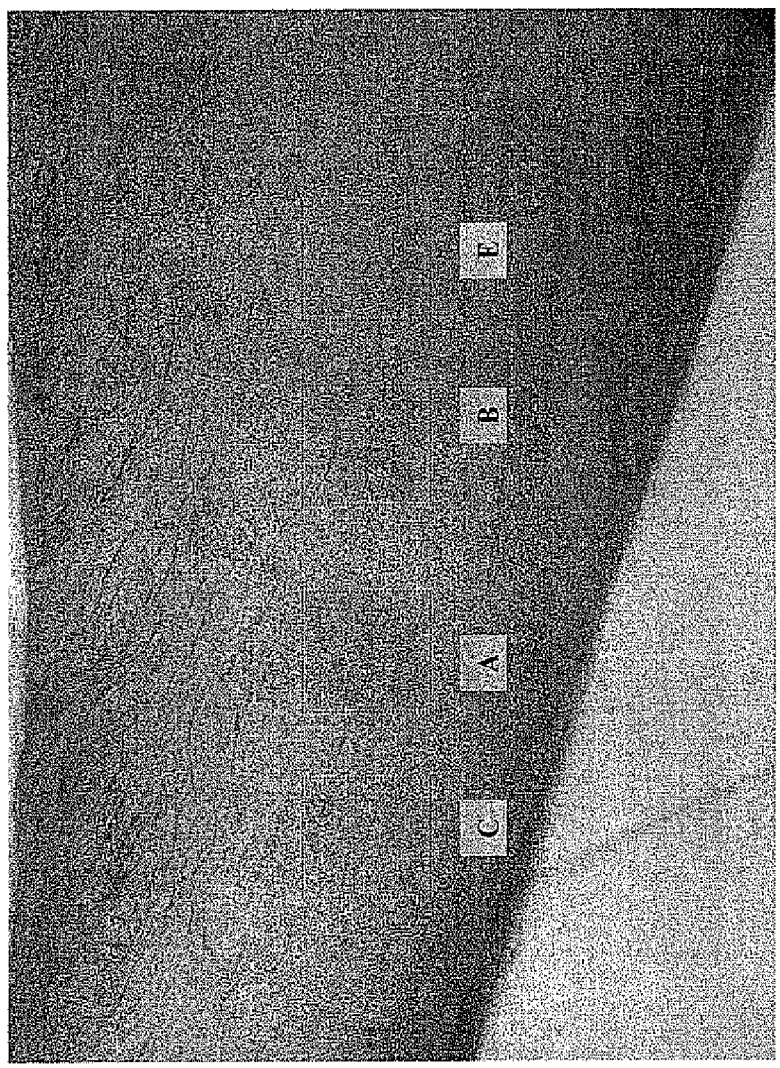
FIG. 1 depicts the irritation test results performed according to Example 6.

The present invention is based on the findings that it is possible to formulate two or more reactive active agents in the same composition. Surprisingly it was found in the present invention that it is possible to formulate a peroxide (preferably benzoyl peroxide) and a retinoid (preferably retinoic acid) which are chemically reactive, in the same composition by coating a solid particulate matter of one of these active agents (or each of these active agents) by a metal oxide coating, thus separating these two active agents from each other in the same composition. Such a composition was found to be advantageous with respect to the chemical stability of the active ingredients and further found to have reduced side effects as compared to a reference composition comprising the uncoated active agents.

Thus, the present invention relates to a composition for topical application comprising as an active ingredient a peroxide and a retinoid wherein one of said peroxide and retinoid is in the form of first microparticles comprising a solid particulate matter of the active ingredient coated by a metal oxide layer and the other of said peroxide and retinoid is present in an uncoated free form or in a coated form of the active ingredient.

As used herein unless otherwise indicated the term "microparticles" refers particles having a core shell structure. It is appreciated that some of the microparticles may at times be formed from two or more core particles of a solid water insoluble particulate matter and may accordingly include, at times, more than one core, such cores being separated from each other by a metal oxide region.

The size of the microparticles (denoted herein also by the general term "particles") as will be referred to herein refers to $D_{90}$ meaning that 90% of the particles have the stated dimension or less (measured by volume). Thus, for examples, for spherical particles stated to have a diameter of 10 micrometer ("microns"), this means that the particles have a $D_{90}$ of 10 microns. The $D_{90}$ (termed also d(0.9)) may be measured by laser diffraction. For particles having a shape other than spheres, the $D_{90}$ refers to the mean average of the diameter of a plurality of particles.

The core (i.e. solid particulate matter) may be of any shape for example rod-like, plate-like, ellipsoidal, cubic, or spherical shape.

In the case of cores having a spherical shape, the diameter ($D_{90}$) may be in the range of 0.3 to 90 microns, preferably 0.3 to 50 microns, more preferably 1 to 50, even more preferably 5 to 30 microns.

By the term "the diameter (D90) may be in the range of 0.3 to 90 microns" is meant that 90% by volume of the particles (in this case the particle's core) may be less than or equal to a value in the range of 0.3 to 90 microns.

For generally cubic-shaped cores or cores having a shape resembling that of a cube, the mean size of a side may be in the range 0.3 to 80 microns, preferably 0.3 to 40 microns, more preferably 0.8 to 40, even more preferably 4 to 15 microns.

For rod-like shaped, ellipsoidal-shaped and plate-like shaped cores, the largest dimension (that of the longest axis) is typically in the range 10 to 100 microns, preferably 15 to 50 microns; and the smallest dimension is typically in the range 0.5 to 20 microns and more preferably 2 to 10 microns.

According to a preferred embodiment of the present invention, the microparticles (coated particulate matter) have a diameter (d90) of 0.5 to 100 µm or preferably the diameter of the microparticles is in the range of 1 to 50 µm and most preferably in the range of 5 to 30 µm. It is appreciated that the microparticles of the present invention are composed of distinct regions of the metal oxide layer in the core material (i.e. the water insoluble particulate matter).

Further according to a preferred embodiment of the present invention the obtained metal oxide coating layer has a width (thickness) of 0.1 micron or above, preferably 0.1-10 micron.

Additionally according to a preferred embodiment of the present invention the obtained metal oxide coating layer has a width (thickness) of 0.3 micron or above, preferably 0.3-10 micron.

Additionally according to a preferred embodiment of the present invention, the thickness of said metal oxide layer is in the range 0.1-10 micron. More preferably 0.1-3 micron, and even more preferably 0.1-1 micron. The thickness of the metal oxide layer may also be preferably in the range 0.3 to 3 micron, and most preferably 0.3 to 2 micron.

Further according to a preferred embodiment of the present invention the obtained metal oxide coating layer has a width (thickness) of about 0.1, 0.2, 0.3, 0.5, 0.7, 1, 1.5, 2 or 5 micron or above, preferably up to 10 micron.

The width of the metal oxide layer may be determined for example by a Transmission Electron Microscope or Confocal Microscope such that in a circular cross sectional area of the particle the smallest width is at least e.g. 0.1 micron (the width is determined as the smallest distance from the surface of the particle (i.e. metal oxide surface) to the core-metal oxide interface).

The microparticles are preferably characterized in that the core material is substantially free of the metal oxide and further in that the metal oxide layer is substantially free of said core material, e.g. either as particle dispersion (in the nano-metric range of below 0.1 µm) of the particulate matter or as molecular dispersion of said particulate matter.

Thus, according to a preferred embodiment of the present invention, the metal oxide layer is substantially free of core material (either in the form of molecules or as nano-metric particles). The term "substantially free" in this context denotes that the concentration of the molecules of the core material or the concentration of the nano-metric particles of the core material is negligible as compared to the metal oxide. Similarly, by the term "the core material is substantially free of the metal oxide" is meant that the concentration of the metal oxide in the core is negligible as compared to the core material. The microparticles (i.e. first microparticles) are preferably non leaching when dispersed in a carrier and most preferably non leaching in an aqueous based carrier.

According to another embodiment when the microparticles are prepared by a method such as spray drying, the core material comprising the active agent may further comprise up to about 30% w/w, preferably up to about 20% metal oxide and the metal oxide coating layer may further comprise up to about 30% w/w, preferably up to about 20% w/w of the active agent.

By the term "non-leaching" it is meant that the leaching of the particulate matter (active agent) from the particles into an aqueous-based liquid is less than 5% w/w, preferably less than 3%, more preferably less than 1% w/w even more preferably less than 0.5% w/w, and most preferably less than 0.1% w/w at room temperature (20° C.), under gentle agitation for 1 hour or until a steady state concentration is achieved. Typically, the aqueous-based liquid is water. The values indicated above refer to the percentage of the active agent leached into an aqueous medium relative to the initial amount of the active agent in the particles. The leaching values indicated above refer preferably to a dispersion having a concentration of the particulate matter in the aqueous medium higher than 0.1% w/w, more preferably higher than 1% w/w, even more preferably higher than 3% w/w, and most preferably higher than 10% w/w. For retinoid the leaching values indicated above refer preferably to a dispersion having a concentration of the particulate matter in the aqueous medium higher than 0.01% w/w.

According to a preferred embodiment of the present invention the weight ratio of said metal oxide to said solid particulate matter is in the range of 1:99 to 50:50. The weight ratio of the metal oxide layer to the solid particulate matter may be also in the range of 3:97 to 50:50, 5:95 to 50:50, 10:90 to 50:50, 5:95 to 30:70, 10:90 to 30:70. Further, according to a preferred embodiment of the present invention the rate ratio of the metal oxide to the solid particulate matter is in the range of 10:90 to 20:80.

According to another preferred embodiment of the present invention, when spray drying method is used, the weight ratio of the metal oxide to said solid particulate matter may be in the range 5:95 to 95:5.

As used herein by the term "uncounted free form" is meant that the active ingredient (peroxide or retenoid) is present in the composition in its "naked" form meaning that it is not intimately embedded, encapsulated, entrapped or encased in a polymeric carrier, and is present in the composition in direct contact with the composition carrier. As used herein by the term "coated form of the active ingredient" is meant that the active ingredient is embedded, dispersed, entrapped, or encased, e.g. as a solid dispersion or molecular dispersion in a polymeric carrier which may be an organic or inorganic carrier and which may serve as a matrix for dispersing the active ingredient or as encapsulated material coating said active ingredient (i.e the active ingredient is present in a core or is a core material encapsulated by a shell composed of a polymeric material which may be an organic or inorganic polymer).

According to a more preferred embodiment of the present invention, said coated form of the active ingredient is second microparticles comprising a solid particulate matter of the active ingredient coated by a metal oxide layer.

Further, according to a preferred embodiment of the present invention, said first microparticles comprise a solid particulate matter of a peroxide coated by a metal oxide layer.

According to a more preferred embodiment of the present invention, said peroxide is in the form of first microparticles comprising solid particulate matter of peroxide coated by a metal oxide layer and said retinoid is in the form of second microparticles comprising a solid particulate matter of the retinoid coated by a metal oxide layer.

The metal oxide coating layer is highly advantageous since it is capable of isolating the particulate matter of the active agent from its surrounding medium, thus preventing cross-reactivity of the active agents present in the same composition and yet enables the release the particulate matter upon application to the surface to be treated.

According to a preferred embodiment of the present invention, the coated form of the active ingredient may be in form of a polymeric microsponge where the active ingredient is adsorbed or entrapped in said microsponge as described for example in U.S. Pat. Nos. 4,690,825; 5,145,675; 5,879,716 and 5,955,109, incorporate herein by reference in their entirety.

As used herein the term "peroxide" refers to a solid water insoluble agent including a peroxide moiety.

The term "solid water insoluble agent" refers to a solid material having solubility in water of less than 3% w/w, typically less than 1% and at times less than 0.5% w/w at room temperature (20° C.). The "solid water insoluble agent" may have a solubility of less than 0.1% w/w.

The "solid water insoluble agent" may also be termed herein as "solid water insoluble particulate matter" or "solid particulate matter".

According to a preferred embodiment of the present invention, the peroxide is benzoyl peroxide.

Additionally, according to a preferred embodiment of the present invention the retinoid is selected from all trans retinoic acid (tretinoin), iso-tretinoin, adapalene, tazarotene, and mixtures thereof.

Thus, the present invention further relates to a composition for topical application comprising as an active ingredient benzoyl peroxide and all trans retinoic acid wherein one of said benzoyl peroxide and all trans retinoic acid is in the form of first microparticles comprising a solid particulate matter of the active ingredient coated by a metal oxide layer and the other of said benzoyl peroxide and all trans retinoic acid is present in an uncoated free form or in a coated form of the active ingredient.

The composition of the present invention comprises a carrier. According to a preferred embodiment of the present invention the carrier is in the form of a ointment, a cream, a lotion, an oil, a solution (preferably an aqueous solution), an emulsion, a gel, a paste, a milk, an aerosol, a powder, or a foam. Preferably the carrier is an aqueous-based carrier (such as a gel, oil-in water emulsion or oil-in water cream, aqueous solution, foam, lotion, spray).

Thus, the final form of the composition may be any of the above forms, mentioned with respect to the carrier, where the microparticles are dispersed in the carrier. The final form of the composition may also be in the form of a wash or cleanser.

Moreover, according to a preferred embodiment of the present invention, the composition having an improved stability as compared to a reference composition the difference between said composition and the reference composition being in that the reference composition and the active ingredients are not coated.

As used herein by the term "improved stability" is meant that the degradation of the retinoid (e.g. tretinoin) in the presence of the peroxide (e.g. benzoyl peroxide) is preferably less than 30%, more preferably less than 20%, even more preferably less than 10% of the initial retinoid concentration in a time range of 3 month at room temperature (20-25° C.), or 1 month at 30° C. Even more preferably degradation of the retinoid (e.g. tritenoin) in the presence of the peroxide (e.g. benzoyl peroxide) is less than 30%, more preferably less than 20%, even more preferably less than 10% of the initial retinoid concentration in the time range of 1 year at room temperature (20-25° C.), or 3 months at 30° C. or 1.5 months at 40° C., and most preferably, degradation of the retinoid (e.g. tritenoin) in the presence of the peroxide (e.g. benzoyl peroxide) is less than 30%, more preferably less than 20%, even more preferably less than 10% of the initial retinoid concentration in the time range of 2 years at room temperature (20-25° C.), or 6 months at 30° C. or 3 months at 40° C. Additionally, according to a preferred embodiment of the present invention, the composition having improved efficacy over individual active ingredients. The individual active ingredients may be in an uncoated free form or in a coated form of the active ingredient as described in the present invention.

According to a preferred embodiment of the present invention the composition further comprising an additional active agent.

Preferably the additional active agent is an antibiotic agent. More preferably the antibiotic agent is an antibiotic of the lincomycin family. Most preferably the antibiotic of the lincomycin family is clindamycin, a pharmaceutical acceptable salt thereof, or an ester thereof.

The antibiotic may be present in an uncoated free form or in a coated form of the active ingredient. The uncoated free form and coated free form may be as described in the present invention with respect to the peroxide and retinoid.

According to a preferred embodiment of the present invention, a composition comprising benzoyl peroxide (BPO), all-trans retinoic acid (ATRA) and an antibiotic as described in the present invention has improved efficacy over at least one of the following combinations: BPO and ATRA, BPO and antibiotics, ATRA and antibiotics.

Preferably, the metal oxide is selected from silica, titania, alumina, zirconia, ZnO, and mixtures thereof. Most preferably the metal oxide is silica.

Moreover according to a preferred embodiment of the present invention, the microparticles (coated particulate matter) have a diameter of 0.5-100 micron. Preferably the particles have a diameter of 0.8-100 micron, more preferably 1-50 micron and most preferably 2-30 micron.

According to certain embodiments of the present invention, the surface of the metal oxide later of the coated particulate matter may be chemically modified by organic groups, preferably hydrophobic groups, attached to its surface.

The hydrophobic groups may be for example an alkyl groups (such alkyl groups may be further substituted with one or more fluoro atoms), aryl groups (such as benzyl or phenyl), and combinations thereof. The groups may be as described below with respect to the process.

Further according to a preferred embodiment of the present invention said first microparticles are prepared by deposition of metal oxide on the surface of the solid particulate matter. The deposition of metal oxide on the surface of the particulate matter may be performed by precipitation of a metal oxide salt onto the surface of the particulate matter, forming a metal oxide layer thereon as will be described below or by a spray drying method.

Preferably the first microparticles are prepared by a process comprising:

(a) contacting the solid, water-insoluble particulate matter, with an ionic additive and an aqueous medium to obtain a dispersion of said particulate matter having positive charges on its surface;

(b) coating the solid, water-insoluble particulate matter, by precipitation of a metal oxide salt onto the surface of the particulate matter, forming a metal oxide coating layer thereon; and (c) aging said coating layer.

Still further according to a preferred embodiment of the present invention said first microparticles are prepared by a process for coating a solid, water-insoluble particulate matter, with a metal oxide comprising:

(a) contacting the solid, water-insoluble particulate matter with an ionic additive and an aqueous medium to obtain a dispersion of said particulate matter having positive charges on its surface;

(b) subjecting the particulate matter to a coating procedure comprising precipitating a metal oxide salt onto the surface of the particulate matter to form a metal oxide layer thereon thereby to obtain particulate matter coated by a metal oxide coating layer;

(c) repeating step (b) at least 4 more times; and (d) aging said coating layer.

In the process described the solid, water-insoluble particulate matter refers to the peroxide or retinoid. The process described may also be used to coat additional active ingredients (e.g. antibiotics) which may be incorporated into the composition described in the present invention.

Step (a) of the process may further comprise reducing the particle size of the particulate matter to the desired particle size for example by milling, or homogenization.

Preferably step (c) of the process described above is repeated 4 to about 1000 times. This means that preferably step (b) of the process described above is repeated 4 to about 1000 times.

Preferably the process comprising repeating step (c) 4 to about 300 times, and more preferably 4 to about 100 times. Even more preferably step (c) of the process described above is repeated 5-80 times and most preferably 5-50 times. This means that preferably step (b) is repeated as indicated above with respect to step (c).

By the term "repeated 4 to about 1000 times" is meant that the process may be repeated 4, 5, 6, 7, 8, 9 etc. times up to and including about 1000 times.

According to a preferred embodiment of the present invention step (d) further comprising after aging, separating the coated particulate matter from the dispersing aqueous medium, such as by filtration, centrifugation or decantation and optionally rinsing and redispersing the obtained coated particulate matter in an aqueous medium.

During the coating process it is preferred that at least 50% of the content the particulate matter (active agent) in the aqueous medium is in a solid state during the coating process.

According to a preferred embodiment of the present invention the process comprising:

(a) contacting the solid, water-insoluble particulate matter, with a first cationic additive and an aqueous medium to obtain a dispersion of said particulate matter having positive charges on its surface;

(b) subjecting the particulate matter to a coating procedure comprising precipitating a metal oxide salt onto the surface of the particulate matter to form a metal oxide coating layer on the particulate matter;

(b1) in an aqueous medium contacting the coated particulate matter with a surface adhering additive being one or both of (i) a second cationic additive, and (ii) a non-ionic additive;

(b2) subjecting the particulate matter obtained in step (b1) to a coating procedure as in step (b);

(c) repeating steps (b1) and (b2) at least 3 more times; and (d) aging the metal oxide coating layer.

Preferably the process comprising repeating step (c) 3 to about 1000 times.

Preferably the process comprising repeating step (c) 3 to about 300 times, and more preferably 3 to about 100 times.

As used herein by the term "repeating step (c) 3 to about 1000 times" is meant that the process may be repeated 3, 4, 5, 6, 7, 8, 9 etc. times up to and including about 1000 times.

Thus, preferably steps (b1) and (b2) are repeated as indicated with respect to step (c).

Additionally according to a preferred embodiment of the present invention the process comprising:

(a) contacting the solid, water-insoluble particulate matter, with an anionic additive, a first cationic additive and an aqueous medium to obtain a dispersion of said particulate matter having positive charges on its surface;

(b) subjecting the particulate matter to a coating procedure comprising precipitating a metal oxide salt onto the surface of the particulate matter to form a metal oxide coating layer on the particulate matter;

(b1) in an aqueous medium contacting the coated particulate matter with one or both of (i) a second cationic additive, and (ii) a non-ionic additive;

(b2) subjecting the particulate matter obtained in step (b1) to a coating procedure as in step (b);

(c) repeating steps (b1) and (b2) at least 3 more times; and (d) aging the metal oxide coating layer.

When an anionic additive and first cationic additive are used in step (a) of the process, preferably the anionic additive is added before the first cationic additive.

Preferably step (c) is repeated 3 to about 1000 times. Preferably step (c) is repeated 3 to about 300 times, and more preferably 3 to about 100 times. This means that preferably steps (b1) and (b2) are repeated as indicted above with respect to step (c).

Step (a) of the process may be conducted for example by (i) contacting the particles with dry ionic additives and then suspending both in an aqueous medium to obtain a dispersion of said particulate matter having positive charges on its surface, or alternatively by (ii) suspending the solid, water-insoluble particulate matter in an aqueous medium comprising ionic additives to obtain a dispersion of said particulate matter having positive charges on its surface.

According to another preferred embodiment of the process may comprise (a) contacting the solid, water-insoluble particulate matter, with an ionic additive selected from (i) an anionic additive; (ii) a first cationic additive, and a combination thereof, and an aqueous medium to obtain a dispersion of said particulate matter having positive charges on its surface; (b), (b1), (b2), (c), (d) are as described herein.

The concentration of the ionic additives in the dispersion can be about 0.001% to about 30%, preferably about 0.01% to about 10% w/w and most preferably about 0.1% up to about 5% w/w. The solid content of the water dispersion can be about 0.1% to about 80% w/w, preferably about 1% to about 60% w/w most preferably about 3% to about 50% w/w.

The purpose of step (a) is to modify the electrical charge of the particulate matter by using ionic additives such that it will be made reactive to the attachment of the metal oxide layer.

For preparing the core material of the particles, the particulate matter ought to be suitably coated with an ionic additive (e.g. cationic additive), such that it can be attached to the precipitated metal oxide salt.

Preferably the ionic additive is selected from a cationic additive, an anionic additive, and a combination thereof. The cationic additive may be a cationic surfactant and/or cationic polymer. The anionic additive may be an anionic surfactant and/or anionic polymer.

The particulate matter is contacted with an ionic additive, for example by mixing it with a solution of a cationic surfactant and/or cationic polymer or an anionic surfactant and a cationic additive (e.g. cationic surfactant and/or cationic polymer). Cationic and anionic surfactants are particularly effective in being adsorbed upon the surface of the particulate matter. The ionic additive may also be anionic polymers used in combination with a cationic additive. The cationic surfactant and/or the cationic polymer and optionally further the anionic surfactant (or anionic polymer) need to be used in sufficient amount to provide positive charges on the surface of the particulate matter. A monolayer of the ionic additive is preferred, but the coating need not be continues. It is sufficient that there are at least spots of cationic additive. These spots will then serve as anchors for the attachment of the metal oxide layer. It is preferred that there are fairly uniform distribution of these anchoring points on the core surface so that as the metal oxide layer builds up it will bridge over and be firmly attached to the core.

According to one preferred embodiment said first and said second cationic additive are the same.

According to another preferred embodiment said first and said second cationic additive are different.

More preferably the first ionic additive is a an anionic surfactant and the second ionic additive is a cationic polymer Most preferably the first cationic additive is a cationic surfactant and the second cationic additive is a cationic polymer.

According to another preferred embodiment, the first cationic additive is a cationic surfactant and the additive in step (b1) is a non-ionic additive (e.g. a non-ionic polymer).

Preferably the coated particulate matter and the second cationic additive are mixed, and most preferable said mixing is under vigorous stirring (e.g. mixer speed above 1000 rpm).

According to a preferred embodiment of the present invention the process further comprising following step (d): (e) separating the coated particulate matter from the aqueous medium and optionally rinsing and redispersing the coated particulate matter in an aqueous medium.

Preferably the separation of the coated particulate matter is conducted by a method such as filtration centrifugation, decantation, dialysis, or by evaporation of the aqueous medium.

Additionally according to a preferred embodiment of the present invention, step (b) comprises adding a metal oxide salt to the aqueous medium; and optionally acidifying the aqueous medium.

Further according to a preferred embodiment of the present invention, step (b2) comprises adding a metal oxide salt to the aqueous medium; and optionally acidifying the aqueous medium.

Preferably step (b1) further comprising adjusting the pH of the dispersion obtained in (b) to a value higher than the isoelectric point of the metal oxide before adding the second cationic additive, more preferably to a pH value of at least about 1 unit higher than the isoelectric point of the metal oxide, before adding the second cationic additive.

Preferably step (b1) further comprising adjusting the pH of the dispersion obtained in (b) to a value higher than the isoelectric point of the metal oxide before adding one or both of (i) a second cationic additive, and (ii) a non-ionic additive, more preferably to a pH value of at least about 1 unit higher than the isoelectric point of the metal oxide, before adding the second cationic additive.

For example, in case the metal oxide is silica (e.g. having an isoelectric point in the range 1.7-2.5) the preferred pH may be at least in the range of about 2.5-6.5.

The purpose of the pH adjustment of the dispersion to a value higher than the isoelectric point of the metal oxide is to form negatively charged metal oxide on the particulate matter surface that will be bound to the positive charges of the second cationic additive thus enabling the attachment of the second cationic additive to the surface of the particulate matter.

The non-ionic additive is of a kind that adheres to the surface ("surface-adherent"). An example is a non-ionic polymer. The non-ionic additive may be used alone or in addition to the second cationic surfactant.

Preferably the particulate matter/metal oxide salt weight ratio, in each of the steps (b) or (b2) is about 5,000/1 to about 20/1, preferably about 5,000/1 to about 30/1, or about 5,000/1 to about 40/1, more preferably about 1,000/1 to about 40/1, and most preferably about 500/1 to about 80/1.

Preferably the particulate matter/cationic additive weight ratio, in step (b1) is about 25,000/1 to about 50/1, preferably about 5,000/1 to about 100/1, and most preferably about 2000/1 to about 200/1.

According to preferred embodiment the particulate matter/metal oxide salt weight ratio, in each of the steps (b) or (b2) is about 5,000/1 to about 65/1, and more preferably about 1000/1 to about 100/1.

Preferably the particulate matter/cationic additive weight ratio, in step (b1) is about 10,000/1 to about 100/1, and more preferably about 5000/1 to about 200/1.

In case a non-ionic additive (e.g. non-ionic polymer) is used alone or in addition to the second cationic additive, the weight ratios of the of the first coated particulate matter to the (i) non-ionic additive or (ii) a combination of a non-ionic additive and second cationic additive, and the weight ratios of the further processed coated particulate matter to the (i) non-ionic additive or (ii) the combination of the non-ionic additive and second cationic additive, may be as indicated above with respect to the second cationic additive.

The aging in step (d) is crucial for obtaining a strengthened and dense layer of metal oxide.

According to a preferred embodiment of the present invention step (d) comprises raising the pH to a value in the range 3-9, preferably to a range of 5-7, and mixing, e.g. by stirring, the suspension (dispersion) in this pH range for a period of e.g. at least 2 h (two hours). Preferably stirring is for 2-96 h, more specifically 2-72 h, more preferably at least 10 h (for example 10-72 h). The stirring is preferably a gentle stirring, preferably in the range 200-500 rpm.

Upon completion of aging, the separation (e.g filtration, centrifugation or decantation) will be easy to perform (due to the hard metal oxide layer formed) and the obtained cake or concentrated dispersion will be easily redispersed in an aqueous medium to form a dispersion of particles.

The purpose of aging in step (d) is to obtain a strengthened and denser layer of metal oxide.

In the absence of the aging step a thinner and softer layer of metal oxide would be obtained since the metal oxide salt upon precipitation forms a gel layer of metal oxide which may disintegrate or erode upon separation and washing or by mechanical stirring.

The aging may be conducted at a temp of 4-90° C., preferably at 15-60° C. and most preferably the aging is conducted at a temperature 20° C.-40° C.

Thus the repeated steps of coating and aging at the end of the process also enable the growth of thicker and stronger layer of metal oxide. Most preferably aging is not conducted between the repeated coating steps (i.e between the repeated coating step (b)), but only at the end of the process. Thus most preferably the aging is conducted only at the end of the process described herein.

Preferably the metal oxide is selected from Silica, Titania, Alumina, Zirconia, ZnO, and mixtures thereof. Most preferably the metal oxide is silica.

The metal oxide salt is preferably an alkali metal oxide salt, e.g. sodium or potassium salt.

According to a preferred embodiment of the present invention the metal oxide salt is selected from sodium silicate, potassium silicate, sodium aluminate, potassium aluminate, sodium titanate, potassium titanate, sodium zirconate, potassium zirconate, and mixtures thereof. Most preferably the metal oxide salt is a silicate salt.

According to certain embodiments, the process may further comprise adding a colloidal metal oxide suspension, preferably aqueous-based suspension (comprising nanometric metal oxide (nanoparticles of metal oxide)) during the coating procedure. Preferably the colloidal metal oxide suspension is selected from colloidal silica suspension, colloidal titania suspension, colloidal alumina suspension, colloidal zirconia suspension, colloidal ZnO suspension, and mixtures thereof. The colloidal metal oxide suspension may be added during the coating process (e.g. in step (b) in one or more of its repeated steps). Preferably the size of the nanometric metal oxide in diameter is in the range between 5-100 nm (average particle size diameter). The weight ratio of the nanometric metal oxide to the metal oxide salt may be in the range 95:5 to 1:99 preferably 80:20 to 5:95 more preferably 70:30 to 10:90, most preferably about 60:40 to 20:80. The weight ratio of the nanometric metal oxide to the metal oxide salt may be about 50:50.

According to other embodiments, the process does not include addition of colloidal metal oxide suspension during the coating process. According to this embodiment nanometric metal oxide particles (nanoparticles of metal oxide) are not added during the coating process.

Further according to a preferred embodiment of the present invention the ionic additive is selected from a cationic surfactant, anionic surfactant, a cationic polymer, and mixtures thereof. When an anionic surfactant is used, preferably a cationic additive is further added such as a cationic surfactant and/or a cationic polymer.

Preferably the cationic additive is selected from a cationic surfactant, a cationic polymer, and mixtures thereof.

According to a preferred embodiment the first cationic additive is a cationic surfactant, and the second cationic additive is a cationic polymer.

The first cationic additive is preferably a cationic surfactant. Preferably the cationic surfactant selected from monoalkylquaternary ammonium salts, dialkyl quaternary ammonium salts, and mixtures thereof.

Preferably the monoalkylquaternary ammonium salts are selected from benzethonium chloride, benzalkonium chloride, cetyltrimethylammonium chloride (CTAC), cetyltrimethylammonium bromide (CTAS), lauryltrimethylammonium chloride, stearyltrimethylammonium chloride, cetylpyridinium chloride, and mixtures thereof.

Most preferably the monoalkylquaternary ammonium salt is cetyltrimethylammonium chloride.

Preferably the dialkyl quaternary ammonium compound is distearyldimethylammonium chloride.

Additional cationic surfactants which can be used are described in: John A. Wenninger et M. (Editors) *International Cosmetic Ingredient Dictionary and Handbook* (Eighth Edition 2000), Vol. 2 pp. 1140-1147, Published by The cosmetic, Toiletry, and Fragnance Association, incorporated herein by reference in its entirety.

The ionic additive may be an anionic surfactant.

Preferably the anionic surfactant is selected from alkyl benzene sulphonic acids and salts, alkyl ether carboxylic acids and salts, alkyl sulphosuccinamates, alkyl sulphossucinates, alpha olefin sulphonates, aromatic hydrocarbon sulphonic acids and salts, fatty alcohol ethoxy sulphates, fatty alcohol sulphates, phosphate esters and mixtures thereof.

Preferably the alkyl benzene sulphonic acid salt is sodium dodecyl benzene sulphonate, the fatty alcohol sulphate is sodium lauryl sulphate, the alkyl sulphossucinates is sodium dioctyl sulphossucinate, and mixtures thereof.

Additional anionic surfactants which can be used are described in: John A. Wenninger et al. (Editors) *International Cosmetic Ingredient Dictionary and Handbook* (Eighth Edition 2000), Vol. 2 pp. 1140-1147, Published by The cosmetic, Toiletry, and Fragnance Association, incorporated herein by reference in its entirety.

Preferably the weight ratio of the ionic additive to the water-insoluble particulate matter is in the range 1:1000-1:10, more preferably in the range 1:200-1:50, most preferably about 1:100. The ratios indicated above refer to an ionic additive such as the first cationic additive or to the combination of a first cationic additive and an anionic additive.

The second cationic additive may be a cationic polymer, a cationic surfactant or mixtures thereof. The cationic surfactant may be as described above.

According to a preferred embodiment of the present invention the second cationic additive is a cationic polymer.

Preferably the weight ratio of the first coated particulate matter (i.e. in step (b1)) to the second cationic additive is in the range of about 25,000/1 to about 50/1, more preferably about 5,000/1 to about 100/1 most preferably about 2000/1 to about 200/1.

Preferably the weight ratio of the further processed coated particulate matter (e.g. in the repeated steps described in step (c)) to the second cationic additive is in the range of about 25,000/1 to about 50/1, more preferably about 5,000/1 to about 100/1, most preferably about 2000/1 to about 200/1.

Preferably the particulate matter/cationic additive weight ratio, in step (b1) is about 10,000/1 to about 100/1, and more preferably about 5000/1 to about 200/1.

Preferably the weight ratio of the further processed coated particulate matter (e.g. in the repeated steps described in step (c)) to the second cationic additive is in the range of about 10,000/1 to about 100/1, and more preferably about 5000/1 to about 200/1.

In case a non-ionic additive (e.g. non-ionic polymer) is used alone or in addition to the second cationic additive, the weight ratios of the of the first coated particulate matter to the (i) non-ionic additive or (ii) a combination of a non-ionic additive and second cationic additive, and the weight ratios of the further processed coated particulate matter to the (i) non-ionic additive or (ii) the combination of the non-ionic additive and second cationic additive, may be as indicated above with respect to the second cationic additive.

Preferably the cationic polymer (of the first cationic additive or second cationic additive) is selected from poly(ethyleneimine) (PEI), poly(dimethyldiallylammonium chloride) (PDAC), poly(acrylamide-co-diallyl-dimethylammonium chloride) (polyquaternium-7), poly(allylamine hydrochloride) (PAH), Chitosan, polylysine, and mixtures thereof.

The second cationic polymer may also be a copolymer of non-ionic and ionic monomers such as pyrrolidone/dimethylaminoethyl methacylate copolymer.

According to another preferred embodiment of the present invention the second cationic additive is selected from colloidal alumina, colloidal ceria (CeO2), colloidal alumina coated silica (such as Ludox CL, Sigma-Aldrich), and mixtures thereof.

The second cationic additive may be a colloidal metal oxide bearing a positive charge such as described above (e.g. colloidal alumina, colloidal ceria (CeO2), colloidal alumina coated silica, or mixtures thereof).

The non-ionic additive used in the process is preferably a non-ionic polymer. The non-ionic polymer may be for example polyvinylalcohol, polyvinylpyrrolidone, and mixtures thereof.

The non-ionic polymer preferably carries hydrogen bonding groups such as hydroxyl, amine groups.

Further according to a preferred embodiment of the present invention, the process further comprises drying the obtained coated particulate matter.

Still further according to a preferred embodiment of the present invention, the drying is by a method selected from spray drying, lyophilization, oven drying, vacuum drying, and fluidized bed.

Still further according to a preferred embodiment of the present invention, the drying is by a method selected from spray drying, lyophilization, oven drying, vacuum drying, and fluidized bed.

Additionally, according to a preferred embodiment of the present invention, the process further comprises chemically modifying the surface of the coated particulate matter.

The surface chemical modification preferably comprises modifying the metal oxide surface with organic groups, preferably hydrophobic groups.

Preferably the process comprising attaching hydrophobic groups to the surface of the metal oxide layer.

The purpose of attaching hydrophobic groups to the surface of the metal oxide layer is to control the water penetration rate into the particles and consequently to control the release of the active agent from the particles. Modifying the surface of the metal oxide layer by hydrophobic groups enables to further control the release of the active agent from the particles, according to the desired rate.

The hydrophobic groups may be for example an alkyl silane, dialkyl silane, trialkyl silane, (such alkyl groups may be further substituted with one or more fluoro atoms), aryl silane (such as benzyl silane, or phenyl silane), diaryl silane, or triaryl silane.

Moreover according to a preferred embodiment of the present invention, the chemical surface modification comprises reacting silanol groups on the surface of the metal oxide layer with precursors selected from monohalotrialkyl silane such as chlortrimethylsilane, dihalodialkyl silane such as dichlorodimethyl silane, trihaloalkyl silane such as trichloromethylsilane, monoalkoxytrialkyl silane such as methoxy tri methyl silane, dialkoxydialkyl silane such as dimethoxydimethylsilane, trialkoxyalkyl silane such as trimethoxymethylsilane, aryltrihalosilane such as phenyltrichlorosilane, diaryldihalosilane such as diphenyldichlorosilane, triarylhalosilane such as triphenylchlorosilane, aryltrialkoxysilane such as phenyltrimethoxysilane, diaryldialkoxysilane such as diphenyldimethoxysilane, triarylalkoxysilane such as triphenylmethoxysilane, and mixtures thereof.

Preferably the alkyl group includes 1-18 carbon atoms, more preferably 1-6 carbon atoms. Most preferably the alkyl is methyl. The alkyl groups may be substituted by one or more fluoro atoms. Preferably the alkoxy group includes 1-6 carbon atoms and more preferably 1-2 carbon atoms.

The halo group may be for example chloro, bromo, iodo, fluoro. Most preferably the halo groups are chloro and bromo.

The aryl is preferably phenyl or benzyl.

The precursors react with the silanol groups on the surface of the metal oxide layer to form a siloxane bond.

The attachment of the hydrophobic groups to the surface of the metal oxide layer can be performed by reacting the dried coated particulate matter with the above precursors. The procedure for attaching hydrophobic groups to the metal can be conducted as follows: a dried powder of coated particulate matter is suspended in an organic solvent such as toluene. A precursor (hydrophobization reagent) from the list above such as dimethyldichlorosilane is added to the organic phase (mixture), optionally in the presence of a halogen scavenger such as trialkyl amine or triethanol amine. The organic mixture is refluxed for at least about 24 hours to obtain coverage of the metal oxide layer with the hydrophobic groups via attachment of the hydrophobic groups to the silanol groups on the surface of the metal oxide layer.

According to certain embodiments the particles (first and/or second microparticles of the invention) may be characterized in that when tested in a Dissolution Tester using Paddle Method in a medium, typically an organic-based solvent such as acetonitrile, isopropyl miristate, ethanol or methanol, in which said particulate matter is soluble, and a dissolution volume in which the concentration of the particulate matter is lower than the solubility of the particulate matter, the time for releasing 50% w/w of the particulate matter from said particles is at least two-fold higher, preferably at least three-fold higher, preferably at least four-fold higher, more preferably at least five-fold higher and most preferably at least ten-fold higher as compared to the dissolution of the free form of the particulate matter having substantially the same particle size diameter as the particulate matter in said particles.

The dissolution of the free form of the particulate matter is measured under the same conditions as the coated particulate matter. The time for releasing 50% w/w of the particulate matter (active agent) from the particles is compared to the time of 50% w/w dissolution of the free form. Preferably the dissolution volume is such that the concentration of the particulate matter is lower than at least half of the solubility of the particulate matter. The "solubility" relates to the solubility of the particulate matter (active ingredient) in the dissolution medium (e.g. an organic-based solvent such as acetonitrile, isopropyl miristate, ethanol or methanol). It is appreciated that the dissolution volume will also depend on the detection level of the analytical method. The dissolution may be conducted at a temperature of 20 C-40 C (20° C.-40° C.). The dissolution may be conducted at a paddle rate of 50-200 rpm.

According to a specific embodiment the dissolution of the particles are as described above, when the particles are prepared by the repetitive coatings steps as described in the process above.

According to certain embodiments the metal oxide layer is substantially not in an amorphous and/or not in a crystalline form. The term "said metal oxide layer is substantially not in an amorphous and/or not in a crystalline form" is meant to denote that distinct regions of amorphous metal oxide (in case the metal oxide in its pure form is amorphous) or crystalline metal oxide (in case the metal oxide in its pure form contains crystalline material, or is purely crystalline) cannot be detected by methods such as X-Ray diffraction. The non-amorphous and/or non-crystalline metal oxide layer refers to a co-structured composite of metal oxide and an adhering additive. Such adhering additive may be for example a polymer which interrupts the formation of continues regions of the metal oxide, thereby leading to the non-amorphous and non crystalline metal oxide form. The non amorphous and non crystalline metal oxide form is characterized by not having any X-ray diffraction peak specific to the metal oxide in its pure form. For example if the metal oxide in its pure form is amorphous, a characteristic X-ray diffraction peak or peaks may be detected. This may be the case, for example, in case of a particle with a pure metal oxide coating. In the case of the particles according to this aspect of the invention, the characteristic X-ray diffraction peak(s), specific to the amorphous form is absent, shifted, or flattened. An example are particles with a silica-based coating, which will have a different peak—namely absent, shifted, or flattened—as compared to particles with an amorphous silica coating. In the case of a metal oxide which in its pure form contains crystalline regions, or is purely crystalline, in the case of a composite coating a peak specific to the crystalline form is absent, shifted, or flattened. Thus, X-ray diffraction may serve to distinguish particles of this aspect of the invention over others.

According to a specific embodiment the metal oxide layer of the particles has the characteristics as described above, when the particles are prepared by the repetitive coating steps as described in the process above.

The first microparticles may also be prepared by a process as disclosed in co-owned PCT application, publication number WO 2007/015243, the content of which is incorporated herein by reference and which is described briefly below:

A process for coating a solid, water-insoluble particulate matter, with a metal oxide comprising:

(a) contacting the solid, water-insoluble particulate matter, with a cationic additive in an aqueous medium to obtain a dispersion of said particulate matter having a positive zeta potential;

(b) coating the solid, water-insoluble particulate matter, by precipitation of a metal oxide salt onto the surface of the particulate matter, forming a metal oxide layer thereon; and (c) aging said coating layer.

The process may comprise subjecting the coated particulate matter to one or more steps of precipitation of metal oxide salt, followed by aging treatment.

In order to obtain a more robust coating, the particles obtained by the above process (following step (c)) may be subject to further, optional, processing steps to cause precipitation of more metal oxide on the initially formed metal oxide layer. Such further processing may include also an aging step, similar to step (c). Additionally, the precipitation step of the additional processing may also involve a step, similar to step (a) above, in which a positive zeta potential is formed on the coating layer (i.e. the metal oxide coating layer), through the addition of a cationic additive, which may be the same or may be different to those used in said step (a). The further processing step may be repeated one, two, three or a plurality of more times.

step (c) may further comprise after aging, separating the coated particulate matter from the dispersing aqueous medium and optionally rinsing and redispersing the obtained coated particulate matter in an aqueous medium.

step (c) may further comprise after redispersing the coated particulate matter in an aqueous medium, adding a second cationic additive to obtain a positive zeta potential of the coating layer.

Alternatively, the further processing steps may be conducted without the addition of a cationic additive. In such a case, the process preferably comprises:

(a) contacting the solid, water-insoluble particulate matter, with a first cationic additive in an aqueous medium to obtain a dispersion of said particulate matter having a positive zeta potential;

(b) coating the solid, water-insoluble particulate matter, by precipitation of a metal oxide salt onto the surface of the particulate matter, forming a metal oxide layer thereon;

(c) aging said coating layer to obtain first coated particulate matter;

(d) coating the first coated particulate matter by precipitation of a metal oxide salt onto the surface of the particulate matter, forming a metal oxide layer thereon; and (e) aging said coating layer to obtain second coated particulate matter;

The process may further comprise:

(f) coating the second coated particulate matter by precipitation of a metal oxide salt onto the surface of the particulate matter, forming a metal oxide layer thereon; and (g) aging said coating layer to obtain third coated particulate matter.

In the absence of a cationic additive in the further processing steps the positive zeta potential in step (a) is preferably less than +150 mV, and more preferably in the range +60 mV to +130 mV. The zeta potential of the coated particulate matter after aging may be in the range 0 mV to −60 mV.

In order to ensure the deposition of further metal oxide layers in the further processing steps by electrostatic interaction and also to control the thickness of the metal oxide (e.g. silica) layers it is preferable to use a second cationic additive.

Preferably the process comprises:

(a) contacting the solid, water-insoluble particulate matter, with a first cationic additive in an aqueous medium to obtain a dispersion of said particulate matter having a positive zeta potential;

(b) coating the solid, water-insoluble particulate matter, by precipitation of a metal oxide salt onto the surface of the particulate matter, forming a metal oxide layer thereon;

(c) aging said coating layer to obtain first coated particulate matter;

(d) contacting the first coated particulate matter with a second cationic additive in an aqueous medium to obtain a dispersion of said first coated particulate matter having a positive zeta potential and further processing the dispersion through steps (b) and (c) to obtain a further processed, coated particulate matter.

The process may further comprise, processing the coated particulate matter obtained in (d) through another step (d).

Preferably the coated particulate matter and the second cationic additive are mixed, and most preferable said mixing is under vigorous stirring (e.g. mixer speed above 1000 rpm).

The first cationic additive used in step (a) of the process has a dual effect: to increase the zeta potential of the particulate matter as will be described below, and also to serve as a wetting agent, thus allowing dispersion of the particulate matter as discrete core particles, where each core particle is individually suspended in the aqueous medium.

It is important that the surface of the particulate matter be reactive or be made subject to bonding with metal oxide layer.

The purpose of step (a) is to modify the zeta potential of the particulate matter by using a cationic additive such that it will be made reactive to the attachment of the metal oxide layer.

For preparing the core material of the particles, the particulate matter ought to be suitably coated with a first cationic additive, such that it can be attached to the precipitated metal oxide salt. The particulate matter is contacted with a first cationic additive, for example by mixing it with a solution of a cationic surfactant or cationic polymer. Cationic surfactants are particularly effective in being adsorbed upon the surface of the particulate matter and they need to be used in sufficient amount to provide a positive zeta potential of the particulate matter (preferably in the range above 0 mV and up to +150 mV, more preferably +60 mV to +130 mV).

A monolayer of the cationic additive is preferred, but the coating need not be continues. It is sufficient that there are at least spots of cationic additive. These spots will then serve as anchors for the attachment of the metal oxide layer. It is preferred that there are fairly uniform distribution of these anchoring points on the core surface so that as the metal oxide layer builds up it will bridge over and be firmly attached to the core.

Preferably the process comprising repeating step (d) one or two additional times, most preferably one additional time.

The first and second cationic additive may be the same or different. Most preferably the first cationic additive is a surfactant and the second cationic additive is a cationic polymer.

Step (c) may further comprise after aging, separating the coated particulate matter from the dispersing aqueous medium and optionally rinsing and redispersing the obtained coated active ingredient in an aqueous medium.

Preferably the separation of the coated particulate matter is conducted by a method such as filtration centrifugation, dialysis, or by evaporation of the aqueous medium.

Step (b) may comprise contacting said dispersion obtained in (a) with a metal oxide salt under conditions so as to precipitate the metal oxide salt onto surface of the particulate matter, yielding a coating layer thereon.

Step (b) may comprises adding a metal oxide salt to yield a value of pH 7-11; and acidifying to yield a pH value of 1-3 (more preferably a pH of about 2).

More preferably step (b) comprises adding a metal oxide salt to reach a value of 8-10; and acidifying to obtain a value of 1-3 (more preferably a pH of about 2).

When the particulate matter is an acidic compound it may be preferred to add a metal oxide salt to reach a pH value of 7-8; and acidifying to obtain a value of 1-3.

Step (b) may further comprise adjusting the pH of the dispersion obtained in (a) to a value in the range 5.5-8 before adding a metal oxide salt, more preferably to a pH value in the range 7-8 before adding a metal oxide salt.

The purpose of the pH adjustment of the dispersion to a value between 5.5-8 is to form negatively charged metal oxide species that will be bound to the positively charged particulate matter surface thus enabling the attachment of the metal oxide layer on the surface of the particulate matter.

Preferably step (b) is repeated at least 1-3 additional times (i.e. one, two or three more times). Most preferably step (b) is repeated one additional time.

The positive zeta potential in step (a) is preferably less than +150 mV (+150 or less, i.e. above 0 and up to +150 mV), and more preferably in the range +60 mV to +130 mV).

Preferably the positive zeta potential in step (d) is less than +150 mV (+150 or less, i.e. above 0 and up to +150 mV), more preferably in the range +5 mV to +130 mV, and most preferably +10 to +100 mV.

The aging in step (c) is crucial for obtaining a strengthened and dense layer of metal oxide.

Preferably step (c) comprises raising the pH to a value in the range 6.5-9.5, preferably to a range of 7.5-8.5, and mixing, e.g. by stirring, the suspension (dispersion) in this pH range for a period of at least 12 h (twelve hours). Preferably stirring is for 12-72 h, more preferably at least 20 h (for example 20-72 h), even more preferably for 36 h-72 h, and most preferably for 40-50 h.

The stirring is preferably a gentle stirring, preferably in the range 200-500 rpm.

An indication for the completion of aging can be obtained by constant zeta potential measurements upon repeated increased dilutions. Further, upon completion of aging, the filtration will be easy to perform (due to the hard metal oxide layer formed) and the obtained cake will be easily redispersed in an aqueous medium to form a dispersion of particles.

The purpose of aging in step (c) is to obtain a strengthened and denser layer of metal oxide and therefore to enable the growth of the metal oxide layer on the core material.

The aging may be conducted at a temp of 4-90° C., preferably at 15-60° C. and most preferably the aging is conducted at a temperature 20° C.-40° C.

Thus the repeated steps of coating and aging also enable the growth of thicker and stronger layer of metal oxide.

Preferably the positive zeta potential in step (a) is less than +150 mV, more preferably zeta potential in the range +60 mV to +130 mV. The preferred zeta potential in step (d) is less than +150 mV, more preferably in the range +5 mV to +130 mV, and most preferably +10 mV to +100 mV. This is the preferred zeta potential also in the further, optional, processing steps.

The metal oxide salt may be as described above.

The cationic additive (i.e. first and/or second cationic additive) may be a cationic surfactant, a cationic polymer, and mixtures thereof. Most preferably the first cationic additive is a cationic surfactant, and the second cationic additive is a cationic polymer.

The first cationic additive is preferably a cationic surfactant.

The cationic surfactant may be monoalkylquaternary ammonium salts, dialkyl quaternary ammonium salts, and mixtures thereof.

The monoalkylquaternary ammonium salts may be benzethonium chloride, benzalkonium chloride, cetyltrimethylammonium chloride (CTAC), cetyltrimethylammonium bromide (CTAS), lauryltrimethylammonium chloride, stearyltrimethylammonium chloride, cetylpyridinium chloride, and mixtures thereof.

Most preferably the monoalkylquaternary ammonium salt is cetyltrimethylammonium chloride.

Preferably the dialkyl quaternary ammonium compound is distearyldimethylammonium chloride.

Additional cationic surfactants which can be used are described in: John A. Wenninger et al. (Editors) *International Cosmetic Ingredient Dictionary and Handbook* (Eighth Edition 2000), Vol. 2 pp. 1140-1147, Published by The cosmetic, Toiletry, and Fragnance Association, incorporated herein by reference in its entirety.

Preferably the weight ratio of the first cationic additive to the water-insoluble particulate matter is in the range 1:1000-1:10, more preferably 1:200-1:50, most preferably about 1:100.

The second cationic additive may be a cationic polymer, a cationic surfactant or mixtures thereof. The cationic surfactant may be as described above.

Preferably the second cationic additive is a cationic polymer. Preferably the weight ratio of the second cationic additive to the first coated particulate matter is in the range 1:1000-1:10, more preferably 1:200-1:50, most preferably about 1:100.

Preferably the weight ratio of the second cationic additive to the further processed coated particulate matter (e.g. second coated particulate matter) is in the range 1:1000-1:10, more preferably 1:200-1:50, most preferably about 1:100.

Preferably the cationic polymer (of the first cationic additive or second cationic additive) is selected from poly(ethyleneimine) (PEI), poly(dimethyldiallylammonium chloride) (PDAC), poly(acrylamide-co-diallyl-dimethylammonium chloride) (polyquatemium-7), poly(allylamine hydrochloride) (PAH), Chitosan, polylysine, and mixtures thereof.

The second cationic additive may be for example colloidal alumina, colloidal ceria (CeO2), colloidal alumina coated silica (such as Ludox CL, Sigma-Aldrich), and mixtures thereof.

The second cationic additive may be for example a colloidal metal oxide bearing a positive charge such as described above (e.g. colloidal alumina, colloidal ceria (CeO2), colloidal alumina coated silica, or mixtures thereof).

The process may further comprise drying the obtained coated particulate matter.

The drying may be conducted by a method selected from spray drying, lyophilization, oven drying, vacuum drying, and fluidized bed.

The first microparticles may also prepared by spray drying as described for example in:

Iskandar, F. et al, Preparation of microencapsulated powders by an aerosol spray method and their optical properties, *Advanced Powder Technol.,* 14(3):349-367, 2003;

Iskandar, F. et al, Control of the morphology of nanostructured particles prepared by the spray drying of a nanoparticle sol, *Journal of Colloid and Interface Science,* 265:296-303, 2003;

Kortesue, P. et al, In vitro evaluation of sol-gel processed spray dried silica gel microspheres as carrier in controlled drug delivery, *International Journal of Pharmaceutics,* 200:223-229, 2003;

Takeuchi, H. et al, Solid dispersion particles of tolbutamide prepared with fine silica particles by the spray-drying method, *Powder Technology,* 141:187-195, 2004;

Kortesuo, P. et al, *Biomaterials,* 23:2795-2801, 2002;

incorporated herein by reference in their entirety.

The second microparticles may also be prepared in the same manner, by the methods described above for the first microparticles.

The peroxide (e.g. BPO) and retinoid (e.g. tritenoin (ATRA)) combination in the same composition can be designed to have differentiation in the release profile of the active agents by modification of the metal oxide (e.g. silica) layer formed on each active agent. Microparticles comprising BPO for example can have a thick silica layer thus providing a slow release profile while microparticles comprising ATRA can have a thin silica layer or the ATRA can have no coating layer at all, thus providing a fast release profile.

The invention additionally relates to a composition for topical application as defined in the present invention the composition having reduced side affects as compared to a reference composition in which the active ingredients are uncoated.

According to a preferred embodiment of the present invention the side effects are selected from irritation, erythema, stringing, itching, scaling, dryness, and combinations thereof.

The side effects may also be other similar dermal undesirable side effect.

The invention further relates to a method for treating a surface condition in a subject comprising topically administering onto the surface a composition as described in the present invention.

Preferably the surface is skin or mucosal membrane. Preferably the surface condition is selected from acne, rosecea, psoreasis, photoaging skin, hyperpigmented skin, mucosal infected areas, inflamed dermatitis, and combinations thereof.

Such surface conditions are preferably treatable by retinoids and peroxides.

Preferably the subject is a mammal and most preferably the mammal is a human.

The term "treating or treatment" as used herein includes any treatment of a condition (disease or disorder such as acne, rosecea, psoreasis, and combinations thereof) associated with a patient's body surface such as the skin or mucosal membrane and includes inhibiting the disease or disorder (i.e. arresting its development), relieving the disease or disorder (i.e. causing regression of the disease or disorder) or relieving the conditions caused by the disease (i.e. symptoms of the disease).

The concentrations of the active ingredients that can be used for treatment of a specific disease or disorder may be 1%-20% w/w BPO and 0.005%-0.5% w/w ATRA, preferably 2.5%-15% w/w BPO and 0.01%-0.2% w/w ATRA, most preferably 2.5%-10% w/w BPO and 0.025%-0.1% w/w ATRA, based on the total weight of the composition. Although individual needs may vary, determination of optimal ranges for effective amounts of the composition is within the skill of the art. Generally, the dosage required to provide an effective amount of a composition which can be adjusted by one skilled in the art will vary depending on the age, health, physical condition, weight, type and extent of the disease or disorder of the recipient, frequency of treatment, the nature of concurrent therapy, if any, and the nature and scope of the desired effect.

Moreover, the present invention relates to a method for preparing a composition comprising as active ingredients a peroxide and a retinoid which are chemically unstable when formulated together, wherein the composition exhibits improved stability of at least one of the active ingredients, the method comprising:

(a) separating said peroxide and retinoid from each other in the composition by coating a solid particulate matter of one of said active ingredients by a metal oxide coating layer to form first microparticles, the other of said peroxide and retinoid is incorporated into the composition in an uncoated free form or in a coated form of the active ingredient; and (b) adding excipients for the preparation of the composition.

As used herein the term "chemical unstable" refers to active ingredients which degrade, decomposes, chemically reacts one with the other resulting in a decrease of the active ingredient initial concentration. The term "chemical unstable" encompasses also "photochemical instability" as a result of light irradiation. Preferably the improved stability refers to the retinoid.

As used herein by the term "separating" is meant that above 90% w/w, preferably above 95% w/w and more preferably above 99% w/w of the total initial amount of the peroxide present in the composition and above 90% w/w, preferably above 95% w/w and more preferably above 99% w/w of the total initial amount of the retinoid present in the composition are separated (i.e. not in direct contact or not intimately mixed) from each other in the same composition.

Preferably, the coated form of the active ingredient is prepared by coating a solid particulate matter of the active ingredient by a metal oxide coating layer to form second microparticles. Preferably the coating is as described in the present invention.

The present invention further relates to a kit comprising: (a) a first composition comprising a peroxide as a first active ingredient; and (b) a second composition comprising a retinoid as a second active ingredient; at least one of said first and said second active ingredient being coated by a metal oxide layer.

Preferably one of the first and the second active ingredient being coated by a metal oxide layer and the other is present in an uncoated free form or in a coated form of the active ingredient.

According to a preferred embodiment the kit further comprising instructions for use in the treatment of a disease or disorder selected from one or more of acne, rosacea, psoriasis, photoaging skin, hyperpigmented skin, inflamed dermatitis, mucosal infected areas, the use comprising combining said first and said second composition for said treatment.

The present invention additionally relates to a method of using the kit as described in the present invention wherein said first composition and said second composition are applied concomitantly or sequentially (one subsequent to the other) onto a surface of a subject's body.

EXAMPLES

In the examples below, all % values referring to a solution are in (w/w).

All % values, referring to dispersions (suspensions) are in (w/w).

Unless otherwise indicated, all solutions used in the example below refer to an aqueous solution of the indicated ingredient.

Example #1

Silica Encapsulation (Coating) of BPO

Step 1: milling: 110 g. of hydrous BPO 75% (USP grade from Sigma, USA) were suspended in 152 g. of 0.4% CTAC solution containing 0.001% silicon antifoam. The BPO was milled using a stator rotor mixer (IKA 6100 operated at 15,000 rpm). The milling was stopped when the particle size distribution (PSD) of the suspension was d(0.9)≤35 µm or the temperature has reached 50 C. The final suspension was cooled to room temperature.

Step 2: coating: During the coating procedure the suspension was stirred with a mechanical dissolver, 60 mm, at 500 RPM at all times. The pH of the milled BPO suspension was corrected to 8 using NaOH 5N solution. A portion of 1 g of 15% sodium silicate solution (15% w/was $SiO_2$) was added and the suspension was stirred for 5 min. A portion of 1 g of 3% Polyquaternium 7 (Poly diallyl ammonium chloride) was added and the suspension was stirred for 5 min. pH was adjusted to 6-7 using 5N HCl solution.

This procedure was repeated for 5-100 times in order to create a series of silica layers around BPO having different thicknesses.

The aging step: The coated BPO suspension at pH 6.5 was kept for aging at room temperature under gentle agitation for 24 hrs.

Example #2

Analytical Evaluation of the BPO Release

The release profile of BPO out of the silica shell was conducted in a water/Acetonitrile solution, which is capable of dissolving BPO. The method is based on the strong oxidation properties of BPO. BPO reacts with $I^-$ ions to form $I_2$, which gives a color reaction. $I_2$ is then reduced back to $I^-$ using sodium thiosulfate (STS) to eliminate the color. Each 12.11 mg of oxidizing BPO can be reduced by 1 ml of 0.1M STS. The evaluation of BPO release was conducted using Solution A and Suspension B as detailed below.

Composition of 100 g. solution A, (capable to distinguish release of 30% BPO): 55 g. Acetonitrile, 12.4 g. 0.1M STS, 4.5 g. KI, 28.1 g. deionized water. Suspension B, preparation of BPO: weigh 200 mg of BPO as 100% (1 g as 20% BPO suspension into 5 ml measuring bottle and fill with deionized water up to 5 ml. Procedure: Into 50 ml glass beaker add 40 ml of solution A and the 5 ml of suspension B. Measure the time for yellow color appearance.

Results:

| Sample | Number of coating cycles | Time for color appearance (min) |
|---|---|---|
| Brevoxyl ™ 8%[a] | Commercial product | 3 |
| NeoBenz ™ 5.5%[b] | Commercial product | 8 |
| SGT-V5, 20%[c] | 5 | 16 |

-continued

| Sample | Number of coating cycles | Time for color appearance (min) |
|---|---|---|
| SGT-V10, 20%[c] | 10 | 37 |
| SGT-V15, 20%[c] | 15 | 108 |
| SGT-V20, 20%[c] | 20 | 152 |

[a]Commercial product containing 8% w/w BPO.
[b]Commercial product containing 5.5% w/w BPO.
[c]Containing 20% w/w BPO in the suspension.
All are normalized to 200 mg BPO in the test method.

Example #3

Silica Encapsulation of Tretinoin

LUDOX TM-50 (purchased from Sigma, USA) is a nanometric suspension of silica (5-20 nm) at pH 9.0. The pH of the Ludox suspension was adjusted to 5-6 using 5N HCl solution. Different amounts of all trans Retinoic acid (Tretinoin) (USP grade from Rhodia) were mixed with pH adjusted Ludox suspension to obtain silica/ATRA ratios of 50/50 up to 90/10 respectively. The suspension was diluted to 20% solids and was milled using a M-110Y microfluidizer processor (Microfluidics) at 15,000 psi. The milling was stopped when the particle size distribution (PSD) of the suspension was d(0.9) ≤5 μm. The temperature was kept below 30 C at all times. The milled suspension was spray dried by a spray drier at inlet temperature of 100 C, outlet temperature of 60 C to obtain silica spheres entrapping tretinoin particles.

Example #4

Analytical Evaluation of the ATRA Release

The release profile of ATRA (Tritinoin) out of the silica shell was done in a water/THF solution at pH=3, which is capable of dissolving ATRA. The amount of released ATRA was measured by titration. All samples contained 0.1 w/w Tritinoin.
Results:

| Sample | Silica/ATRA ratio | Time for titration of 30% ARTA (min) |
|---|---|---|
| Retin A ™ 0.1% | Commercial product | 5 |
| Retin A Micro ™ 0.1% | Commercial product | 13 |
| SGT-T50, 0.1% | 50/50 | 24 |
| SGT-T30, 0.1% | 70/30 | 40 |
| SGT-T10, 0.1% | 90/10 | 57 |

Example #5

Stability Study of BPO/ATRA Mixture

A water based gel formulation containing 5% BPO and 0.1% ATRA was prepared using free and encapsulated active agents. The following mixtures were prepared using samples from examples 2 and 4:

| Sample # | BPO | ATRA |
|---|---|---|
| A | Non-encapsulated | Non-encapsulated |
| B | SGT-V20 | Non-encapsulated |
| C | SGT-V20 | SGT-T50 |
| D | SGT-V5 | SGT-T10 |
| E | SGT-V20 | SGT-T10 |
| F | Non-encapsulated | SGT-T10 |

The gels were placed for stability at the following temperatures: 4 C, 25 C and 30 C and the degradation in ATM concentration was measured.
Results:

| Sample # | Degradation of ATRA as % from initial concentration | | | | | | | | |
|---|---|---|---|---|---|---|---|---|---|
| | 4 C | | | 25 C | | | 30 C | | |
| | 1* | 2 | 3 | 1 | 2 | 3 | 1 | 2 | 3 |
| A | 13.1 | 33.9 | 59.1 | 83.5 | 100 | — | 100 | — | — |
| B | 0.5 | 0.8 | 1.2 | 4.5 | 8.8 | 17.3 | 29.5 | 100 | — |
| C | 0.3 | 0.5 | 0.9 | 2.8 | 7.1 | 12.4 | 27.3 | 100 | — |
| D | 0.6 | 1.1 | 1.9 | 6.2 | 13.9 | 27.1 | 55.3 | 100 | — |
| E | 0.1 | 0.1 | 0.3 | 1.8 | 3.4 | 6.9 | 9.1 | 20.5 | 54.3 |
| F | 2.3 | 4.9 | 9.7 | 31.8 | 78.3 | 100 | 65.1 | 100 | — |

*Time in months

It is clearly shown that the encapsulation of the APIs (active pharmaceutical ingredients) increases dramatically the stability of ATRA. The most stable combination is mixture E in which both BPO and ATRA have the longest release time. The encapsulation of BPO is more significant to the stability than that of ATRA.

Example #6

In-house Irritation Patch Test

The water based gel formulations from example #5 were tested in a 4 hrs patch test. The compounds were applied once during the study, at time 0. Removal of the patches was after 4 hrs. Observation and pictures of the application areas (FIG. 1) were taken after additional 24 hrs (total 28 hrs).

The picture shows the irritation caused by samples A, B, C and E. The strong irritation of the non-encapsulated sample (A) is clearly shown. Sample B has much lower irritation whereas samples C and E are completely non-irritant.

Example #7

Silica Encapsulation of Tretinoin

Step 1: milling: 75 g. of all trans Retinoic acid (Tretinoin) (USP grade from Rhodia) were suspended in 250 g. of 0.3% CTAC solution containing 0.001% silicon antifoarn. The ATRA was milled using a M-110Y microfluidizer processor (Microfluidics) at 15,000 psi. The milling was stopped when the particle size distribution (PSD) of the suspension was d(0.9)≤20 μm. The temperature has kept below 30 C at all times.

Step 2: coating: During the coating procedure the suspension was stirred with a mechanical dissolver, 60 mm, at 500 RPM at all times. The pH of the milled ATRA suspension was corrected to about 4 using HCl 5N solution. A portion of 0.5 g of 15% sodium silicate solution (15% w/w as $SiO_2$) was added and the suspension was stirred for 5 min. A portion of 0.5 g of 3% Polyquaternium 7 was added and the suspension was stirred for 5 min. pH was readjusted to about 4 using 5N HCl solution. This procedure was repeated for 5-100 times in order to create a series of silica layers around ATRA having different thicknesses.

The aging step: The coated ATRA suspension at pH 4.5 was kept for aging at room temperature under gentle agitation for 24 hrs.

Example #8

Silica Encapsulation of Tazarotene (TAZ)

Step 1: milling: 50 g. of Tazarotene (from Glenmark) were suspended in 350 g. of 0.3% CTAC solution containing 0.001% silicon antifoam. The TAZ was milled using a M-110Y microfluidizer processor (Microfluidics) at 15,000 psi. The milling was stopped when the particle size distribution (PSD) of the suspension was d(0.9)≤25 μm. The temperature was kept below 30 C at all times.

Step 2: coating: During the coating procedure the suspension was stirred with a mechanical dissolver, 60 mm, at 500 RPM at all times. The pH of the milled TAZ suspension was corrected to about 3 using HCl 5N solution. A portion of 1 g of 15% sodium silicate solution (15% w/w as $SiO_2$) was added and the suspension was stirred for 5 min, A portion of 0.3 g of 3% Polyquaternium-1 was added and the suspension was stirred for 5 min. pH was readjusted to about 3 using 5N HCl solution.

This procedure was repeated for 50 times in order to create silica layers around TAZ.

The aging step: The coated TAZ suspension at pH 4.5 was kept for aging at room temperature under gentle agitation for 24 hrs.

Example #9

Tretinoin Stability Test 1.0 Method Objective and Principle

The ATRA (All-trans-Retinoic acid) was tested for stability in presence of Benzoyl peroxide (BPO) at a ratio of 0.1% ATRA to 6% BPO. The stability screening was performed in water: ATRA and BPO were re-suspended in water for 4 hours at 40° C. (testing time zero and 4 hours, or other). At the end of the procedure the ATRA was extracted with dilution solution containing BHT (for better stability of sample preparation) and determined using HPLC method against external standard at 352 nm.

2.0 Reagents and Equipments
Acetonitrile: HPLC grade
Water: HPLC grade
Isopropyl alcohol (IPA): HPLC grade
Glacial acetic acid: HPLC grade
Butylated hydroxytoluene (BHT): Analytical grade
Column: Zorbax RX-C18 3.5 μm 4.6*150 mm
Fluent: 70% Acetonitrile and 30% of 1% Acetic acid in Water
Flow rate: 1.3 ml/min.
Detection: UV, Wavelength 352 nm.
Injection Volume: 10 μL
Column Temperature: 40° C.
2.1 Dilution Solution Preparation
Dissolve 1 g of BHT in 1000 ml of Acetonitrile.
3.0 ATRA Standard Preparation
Weight approximately 50 mg of ATRA RS into a 50 ml low actinic volumetric flask add about 30 ml of IPA. Sonicate for 10 min, cool to room temperature and fill to volume (Stock solution). Transfer 2 ml of stock solution to a 50 ml low actinic volumetric flask, fill to volume with dilution solution (solution S).
4.0 System Suitability Solution
See ATRA Standard Preparation.
5.0 Sample Preparation
Fill a 3 ml Pasteur pipette with sample. Transfer the pipette content to a previously weighed 50 ml volumetric flask. Weigh the flask, add 30 ml of dilution solution, and sonicate for 15 minutes (avoid heating). Fill to volume with dilution solution, and filter through 0.2μ Nylon Syringe Filter, discard the first ml (solution A).
6.0 Procedure
Samples and standards should be prepared in duplicates.
Sample and Standard Preparation should be prepared and sampled at the same temperature.
7.0 Calculation
Calculate the ATRA assay in the sample using the formula:

$$\% \ ATRA = \frac{Asample * Cstd * \% \ Pstd}{Astd * Csample}$$

Where:
Asample—ATRA peak area arising from the Sample Preparation.
Astd—ATRA peak area arising from the Standard Preparation.
Csample—Sample Concentration in mg/ml.
Cstd—Standard Concentration in mg/ml.
% Pstd—% Purity of the standard

Example #10

Coating Using Sodium Silicate and a Polymer

Tretinoin crystals were encapsulated with several cycles of sodium silicate and either PVA (polyvinyl alcohol) or PDAC-7 (polyquatrnium-7). The cycles each consisted of the following steps: first, sodium silicate was added until the pH reached 7; the solution was then acidified with HCl (usually 1 M solution) to pH 3, at which point the polycation or non-ionic polymer was added. After the last cycle, a final layer of sodium silicate and HCl was applied. On several occasions, Ludox TM 50 (Grace davision, USA) (2.5%) was added to the sodium silicate solution for the coating. BHT (butylated hydroxytuluene) was added in some cases to the tretinoin before the milling process as an anti-oxidant. 5% tretinoin in water containing 0.3% CTAC was used in all cases was milled in a microfluidizer (d (0.9)≤12-13 μm). Stability of the encapsulated tretinoin crystals was checked with a BPO solution as described in example #9.

Results

Figure 2:
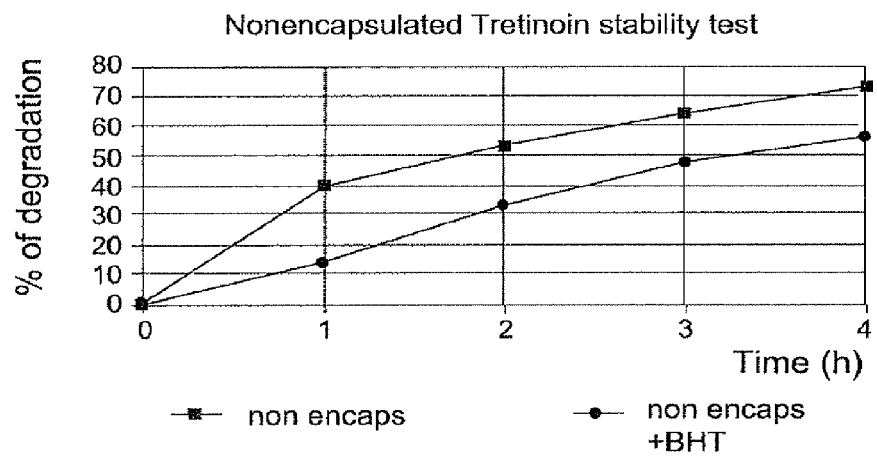

An assortment of coatings on the tretinoin crystals was performed. At first we compared the degradation of the tretinoin when coated with 10 cycles of sodium silicate (2.5%) and PDAC-7 with and without BHT. It was found that the addition of BHT prevented the degradation of tretinoin by 15-20% (FIG. 2). Therefore, all further experiments were conducted with the addition of BHT.

In order to obtain better stability with BPO, we compared two polymers: PDAC-7 and PVA. Generally the PDAC-7 gave slightly better stability results.

The results show that the more coating cycles performed, the better the stability of the active ingredients. For example, the comparison between 15 to 30 cycles shows that when increasing the number of cycles, the stability grows.

Figure 3:
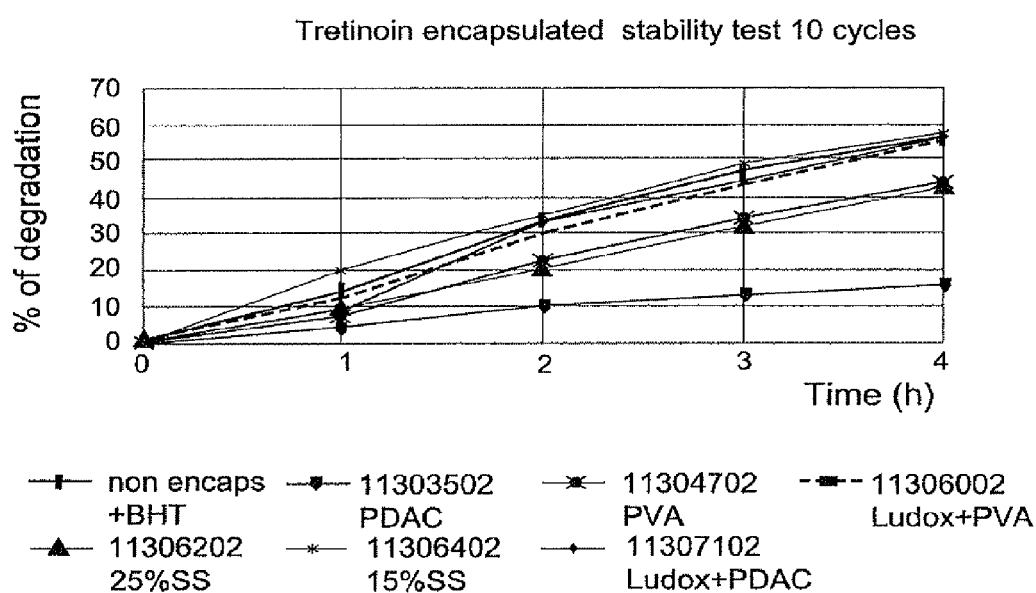
FIG. 3: shows the stability results for tretinoin encapsulated by 10 cycles, under assorted conditions.

The addition of Ludox (TM-50) to the sodium silicate solution to give a 2.5% w/w solution of S.S. (Sodium Silicate) and 2.5% w/w Ludox, each, usually resulted with better stability. Without being bound to theory, this is perhaps the result of the fact that the Ludox supplies partially formed silica to the shell, which does not always form completely when only sodium silicate is used. This can be seen in FIG. 3.

Conclusions

It is evident from the results that were obtained that in order to achieve better stability the number of coating cycles should be increased.

TABLE 1

Summary of the stability experiments.

| Sample | BHT | # Of cycles | Ludox | Polymer | Remarks | % Degradation as measured by example #9[a] |
|---|---|---|---|---|---|---|
| 11303002 | − | 10 | − | PDAC | | 33.1 |
| 11303502 | + | 10 | − | PDAC | | 15.7 |
| 11304402 | − | 5 | − | PVA | | 78.1 |
| 11304502 | − | 10 | − | PVA | | 62.6 |
| 11304702 | + | 10 | − | PVA | | 42.8 |
| 11305202 | + | 15 | − | PVA | | 69.2 |
| 11306002 | + | 10 | + | PVA | | 56.1 |
| 11306202 | + | 10 | − | PDAC | | 42.8 |
| 11306402 | + | 10 | − | PDAC | | 57.7 |
| 11306902 | + | 30 | + | PVA | | 40.7 |
| 11307002 | + | 50 | + | PVA | | 24.2 |
| 11307102 | + | 10 | + | PDAC | | 56.1 |
| 11307502 | + | 15 | + | PDAC | | 58.7 |
| 11307503 | + | 30 | + | PDAC | 11307502 filtered and then repeated | 37.9 |

[a] after four hours at 40° C. at pH 5.

Figure 4:
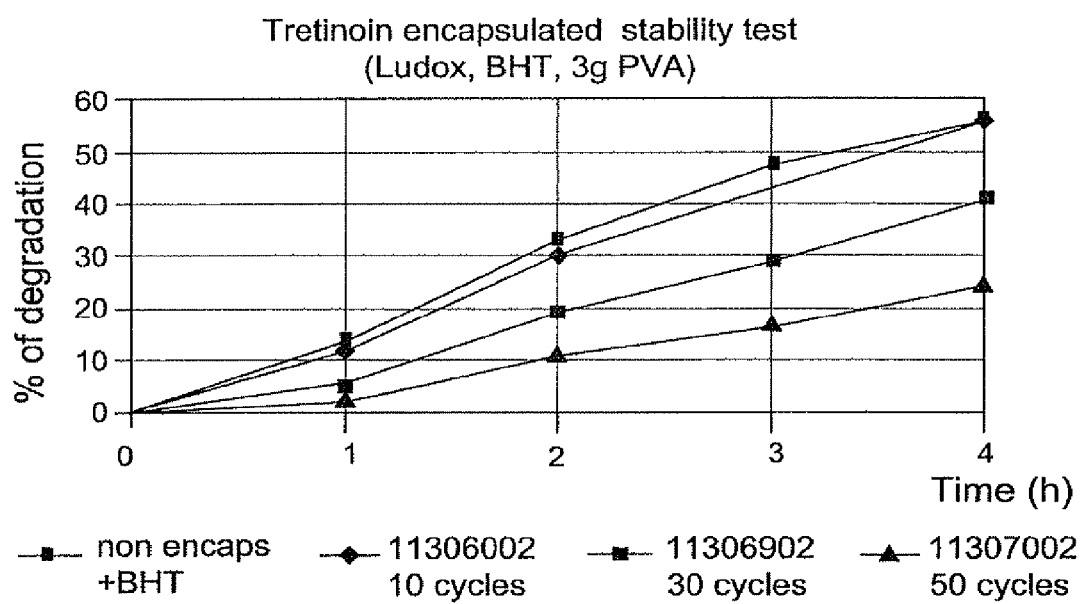
FIG. 4: shows the influence of the number of coating cycles on the stability of the encapsulated tretinoin.

The results are also shown in FIG. 4.

Method of determining coated Tretinoin release profile (assay method (#03/1-AS-01))

Method Principle

To evaluate the release of ATRA (All-trans-Retinoic acid) from encapsulated product. The encapsulated ATRA product was extracted by a biphasic extraction system, by re-suspending ATRA product in a buffer/IPM (isopropylmeristate) at room temperature and tested at time zero and every few hours, or other. At the end of the procedure the ATRA was determined by HPLC method against external standard at 352 nm.

The reagents, equipments, standard and sample preparations, and analytical procedures used are detailed in example #9.

Sample Preparation

Transfer a quantity of encapsulated ATRA product, equivalent to about 20 mg of ATRA, to a 250 ml amber Erlenmayer flask. Add 100 ml of phosphate buffer, mix. Add 100 ml of IPM and stir on a magnetic stirring plate at 500 rpm. Remove 1.0 ml of upper layer at different time intervals into eppendorf. Centrifuge for 10 minutes at 10000 rpm. Transfer 0.5 ml of clear liquid into 25 ml amber volumetric flask, dilute to volume with Acetonitrile and filter through 0.2μ Nylon Syringe Filter, discard the first ml (solution A).

Calculation

Calculate the % of ATRA released using the formulas:

$$\% \text{ released} = \frac{\% \text{ ATRA}}{\text{Assay (\%)}} * 100$$

Where:
Assay(%)—content of ATRA in the sample according to assay method (#03/1-AS-01).

$$\% \text{ ATRA} = \frac{A_{sample} * C_{std} * \% \ P_{std}}{A_{std} * C_{sample}}$$

The parameters Asample, Cstd, % Pstd, Astd, Csample are described above in Example #9 under "calculation".

While this invention has been shown and described with reference to preferred embodiments thereof, it will be understood by those skilled in the art that many alternatives, modifications and variations may be made thereto without departing from the spirit and scope of the invention. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference.

The invention claimed is:

1. A composition for topical application comprising as active ingredients
    a solid particulate matter of a peroxide, and
    a solid particulate matter of a retinoid; wherein
        at least one of the active ingredients is in the form of first microparticles, and
        each microparticle of the first microparticles contains one or more solid cores consisting of either the solid particulate matter of the peroxide or the solid particulate matter of the retinoid, the one or more solid cores being coated by a metal oxide layer.

2. The composition of claim 1, further comprising second microparticles having a solid core consisting of either
    the solid particulate matter of the peroxide, or
    the solid particulate matter of the retinoid, wherein the solid core of each second microparticle is coated by a metal oxide layer.

3. The composition of claim 1, wherein said first microparticles comprise the solid particulate matter of the peroxide coated by a metal oxide layer.

4. The composition of claim 1, wherein the first microparticles have a solid core consisting of the solid particulate matter of the peroxide, the solid core of the first microparticles being coated by a metal oxide layer, and
    the composition further comprises second microparticles having a solid core consisting of the solid particulate matter of the retinoid, the solid core of the second microparticles being coated by a metal oxide layer.

5. The composition of claim 1, wherein said peroxide is benzoyl peroxide.

6. The composition of claim 1, wherein said retinoid is selected from all trans retinoic acid, iso-tretinoin, adapalene, tazarotene, and mixtures thereof.

7. The composition of claim 1 having an improved stability as compared to a reference composition the difference between said composition and the reference composition being in that in the reference composition the active ingredients are not coated.

8. The composition according to claim 1 further comprising an additional active agent.

9. The composition of claim 1, further comprising an antibiotic agent.

10. The composition according to claim 1, wherein said metal oxide is selected from silica, titania, alumina, zirconia, ZnO, and mixtures thereof.

11. The composition according to claim 1, wherein said metal oxide is silica.

12. A composition for topical application comprising as active ingredients
   a solid particulate matter of benzoyl peroxide, and
   a solid particulate matter of all trans retinoic acid, wherein
      at least one of the active ingredients is in the form of first microparticles, and
      each microparticle of the first microparticles contains a solid core consisting of either the solid particulate matter of benzoyl peroxide or the solid particulate matter of all trans retinoic acid, the solid core being coated by a metal oxide layer.

13. A composition according to claim 1, wherein said retinoid is tazarotene.

14. The composition according to claim 12, wherein said first microparticles are prepared by deposition of metal oxide on the surface of either
   the solid particulate matter of benzoyl peroxide, or
   the solid particulate matter of all trans retinoic acid.

15. The composition according to claim 12, wherein said first microparticles are prepared by (a) contacting a solid, water-insoluble particulate matter, with an ionic additive and an aqueous medium to obtain a dispersion of said water-insoluble particulate matter having positive charges on its surface;

(b) coating a solid, water-insoluble particulate matter, by precipitation of a metal oxide salt onto the surface of the water-insoluble particulate matter, forming a metal oxide coating layer thereon; and (c) aging said coating layer.

16. A composition according to claim 12, said composition having reduced topical side effects as compared to a reference composition in which the active ingredients are uncoated.

17. A kit comprising:
   (a) a first composition comprising a peroxide as a first active ingredient; and
   (b) a second composition comprising a retinoid as a second active ingredient; wherein
      at least one of said first and said second active ingredient is present in a solid core of a microparticle, the solid core being coated by a metal oxide layer, and
      the solid core of the microparticle consisting of either said first active ingredient, or said second active ingredient.

18. The kit of claim 17 wherein at least one of said first and said second active ingredient is present in an uncoated free form.

19. The kit of claim 17, further comprising instructions for use in the treatment of a disease or disorder selected from one or more of acne, rosacea, psoriasis, photoaging skin, hyperpigmented skin, inflamed dermatitis, mucosal infected areas, the use comprising combining said first and said second composition for said treatment.

* * * * *